United States Patent
Nguyen et al.

(10) Patent No.: US 12,016,524 B2
(45) Date of Patent: Jun. 25, 2024

(54) ROTATABLE MEDICAL DEVICE

(71) Applicant: Boston Scientific Scimed, Inc., Maple Grove, MN (US)

(72) Inventors: Man Minh Nguyen, Harvard, MA (US); Scott E. Brechbiel, Acton, MA (US); Evan Wilder, Boston, MA (US); James Weldon, Newton, MA (US); Sean Powell, Holden, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 493 days.

(21) Appl. No.: 17/137,556

(22) Filed: Dec. 30, 2020

(65) Prior Publication Data

US 2021/0212556 A1      Jul. 15, 2021

Related U.S. Application Data

(60) Provisional application No. 62/958,788, filed on Jan. 9, 2020.

(51) Int. Cl.
*A61B 1/00* (2006.01)
*A61B 1/267* (2006.01)
(Continued)

(52) U.S. Cl.
CPC ...... *A61B 1/00066* (2013.01); *A61B 1/00147* (2013.01); *A61B 1/2676* (2013.01);
(Continued)

(58) Field of Classification Search
CPC . A61B 1/0006; A61B 1/00147; A61B 1/2676; A61B 1/2736; A61B 1/307;
(Continued)

(56) References Cited

U.S. PATENT DOCUMENTS 5,330,501 A * 7/1994 Tovey ............... A61B 17/3421
604/164.11
5,836,960 A   11/1998 Kolesa et al.
(Continued)

FOREIGN PATENT DOCUMENTS

EP      2635205 A1   9/2013
EP      3476311 A1   5/2019
WO   2016168537 A1  10/2016

OTHER PUBLICATIONS

Evis Exera III BF-190 Bronchoscopes, Olympus America [retrieved on Dec. 28, 2020]. Retrieved from the Internet: <URL: https://medical.olympusamerica.com/products/bf-190>.
(Continued)

*Primary Examiner* — John P Leubecker
*Assistant Examiner* — Li-Ting Song
(74) *Attorney, Agent, or Firm* — Bookoff McAndrews PLLC

(57) ABSTRACT

Medical devices and related methods are described. The medical device may include a shaft, a handle housing a proximal portion of the shaft, and a lock having a first configuration and a second configuration. In the first configuration of the lock, the shaft may be rotatable about a longitudinal axis of the shaft relative to the handle, and, in the second configuration of the lock, the shaft may be stationary relative to the handle.

17 Claims, 23 Drawing Sheets

(51) Int. Cl.
  *A61B 1/273* (2006.01)
  *A61B 1/307* (2006.01)
  *A61B 1/31* (2006.01)
(52) U.S. Cl.
  CPC ............ *A61B 1/2736* (2013.01); *A61B 1/307* (2013.01); *A61B 1/31* (2013.01)
(58) Field of Classification Search
  CPC ............ A61B 1/31; A61B 2017/0034; A61B 2090/0811; A61B 1/00128; A61B 2017/2946; A61B 1/0052; A61B 2017/2929
  USPC ......................................................... 600/137
  See application file for complete search history.

(56) References Cited

U.S. PATENT DOCUMENTS

| | | | | |
|---|---|---|---|---|
| 6,077,286 | A | | 6/2000 | Cuschieri et al. |
| 6,139,214 | A | * | 10/2000 | Zirps .......................... F16D 1/10 403/328 |
| 7,824,327 | B2 | * | 11/2010 | Smith ................ A61B 1/00154 606/1 |
| 8,475,362 | B2 | * | 7/2013 | Sohn .................. A61B 17/3423 600/137 |
| 10,874,290 | B2 | * | 12/2020 | Walen ................ A61B 17/1631 |
| 2007/0287993 | A1 | * | 12/2007 | Hinman ................. A61B 17/29 606/1 |
| 2008/0154299 | A1 | * | 6/2008 | Livneh ............... A61B 17/2909 606/205 |
| 2008/0244913 | A1 | * | 10/2008 | Lin .......................... B25D 3/00 30/167 |
| 2009/0261536 | A1 | * | 10/2009 | Beale ..................... B23B 31/22 279/19.7 |
| 2014/0066700 | A1 | | 3/2014 | Wilson et al. |
| 2014/0371728 | A1 | * | 12/2014 | Vaughn .................. B23B 31/22 606/1 |
| 2016/0302840 | A1 | * | 10/2016 | Scheib .................. A61B 18/00 |
| 2017/0078583 | A1 | * | 3/2017 | Haggerty ............... H04N 23/55 |
| 2018/0161060 | A1 | | 6/2018 | Roberson et al. |
| 2018/0242962 | A1 | * | 8/2018 | Walen ............ A61B 17/320758 |
| 2019/0125475 | A1 | * | 5/2019 | Wise ...................... A61B 90/03 |

OTHER PUBLICATIONS

International Search Report dated Apr. 12, 2021 in Application No. PCT/US2020/067407 (15 pages).

* cited by examiner

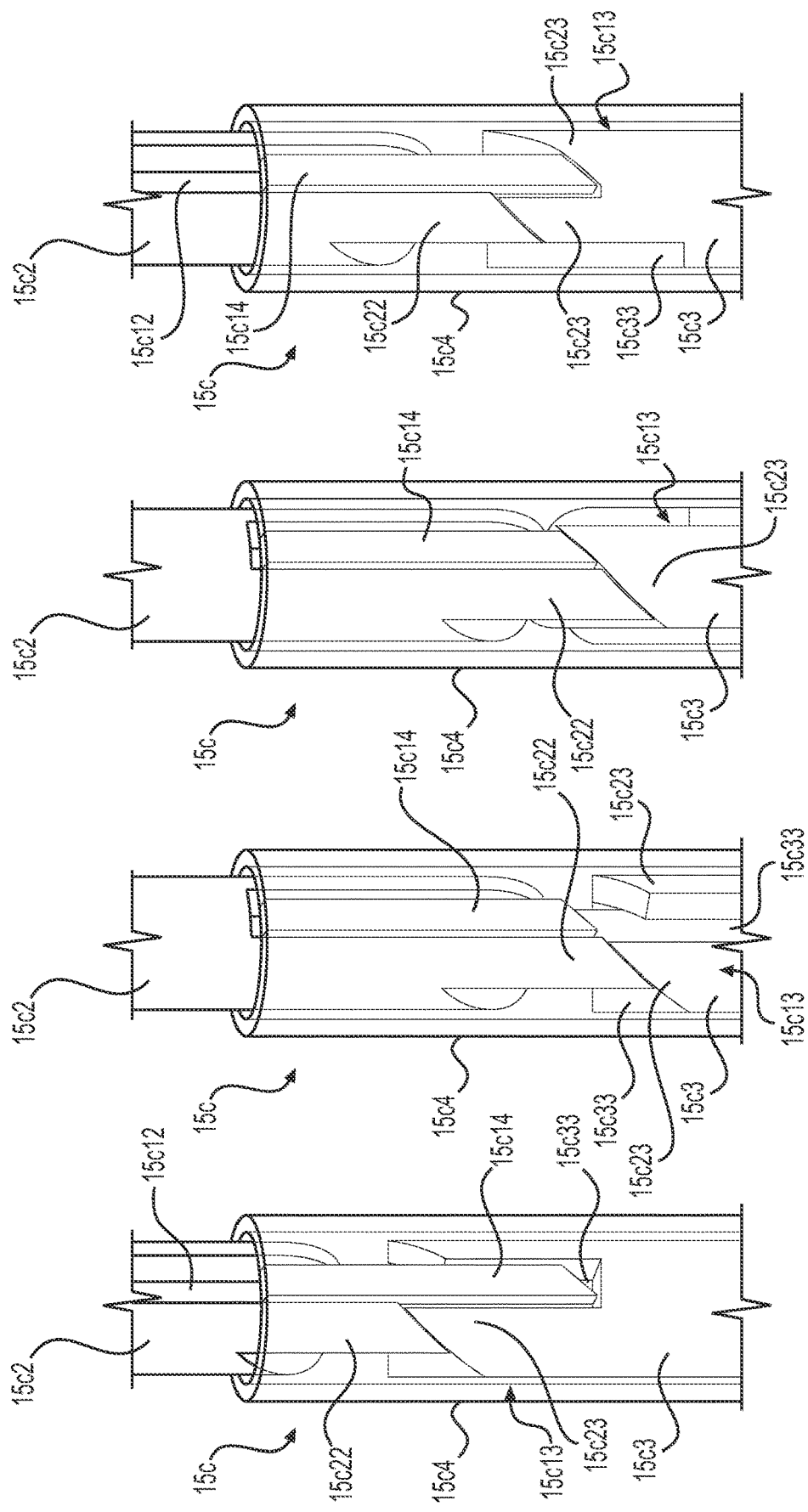

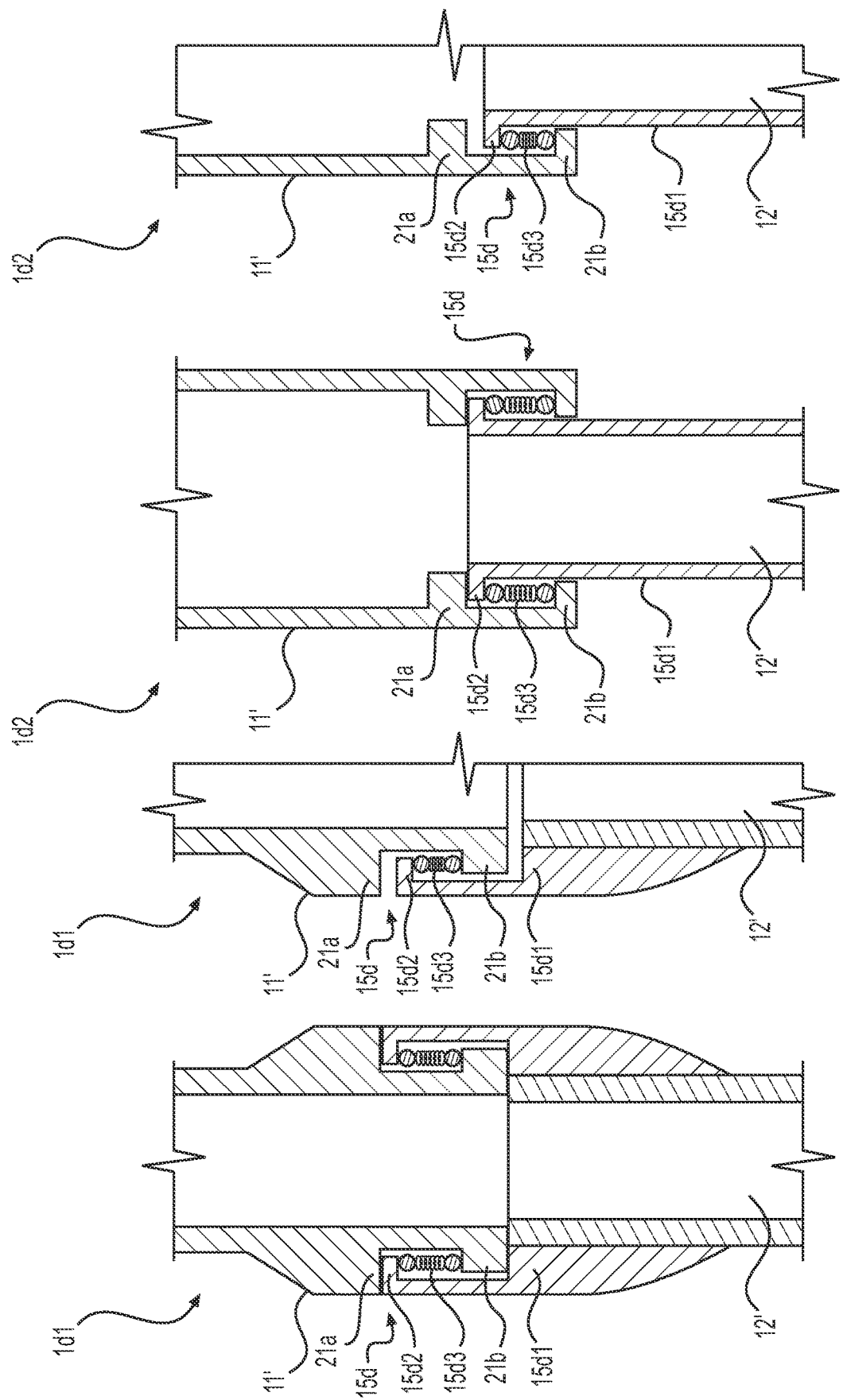

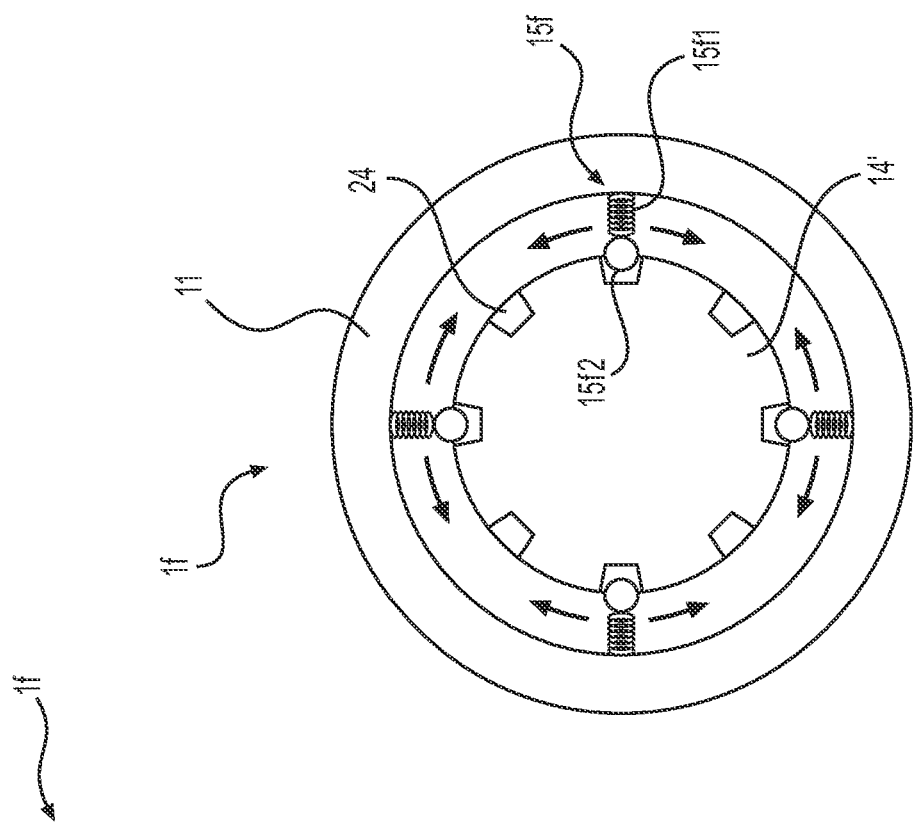
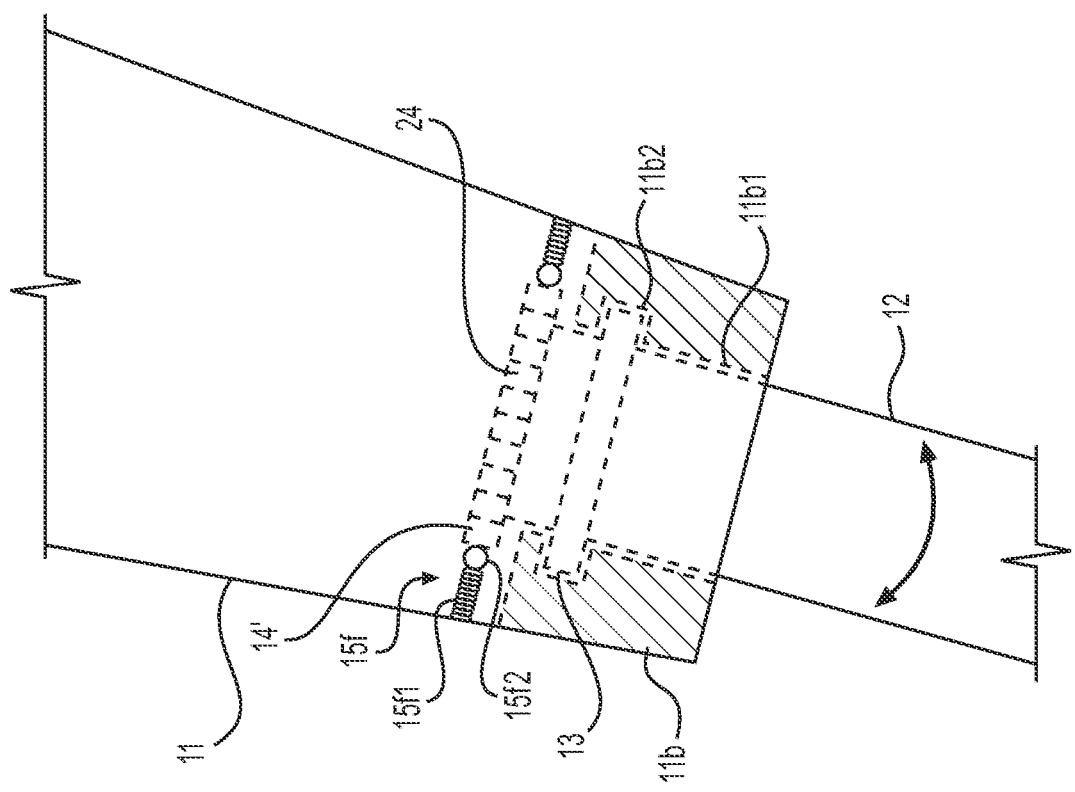
FIG. 6A
FIG. 6B

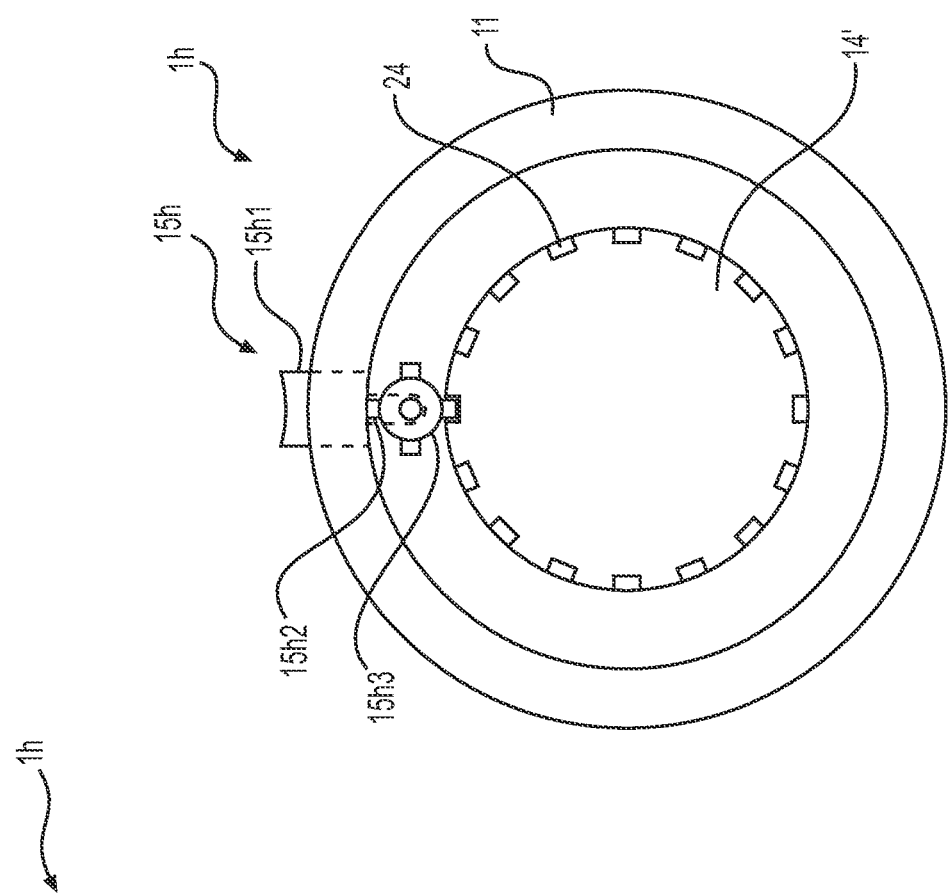
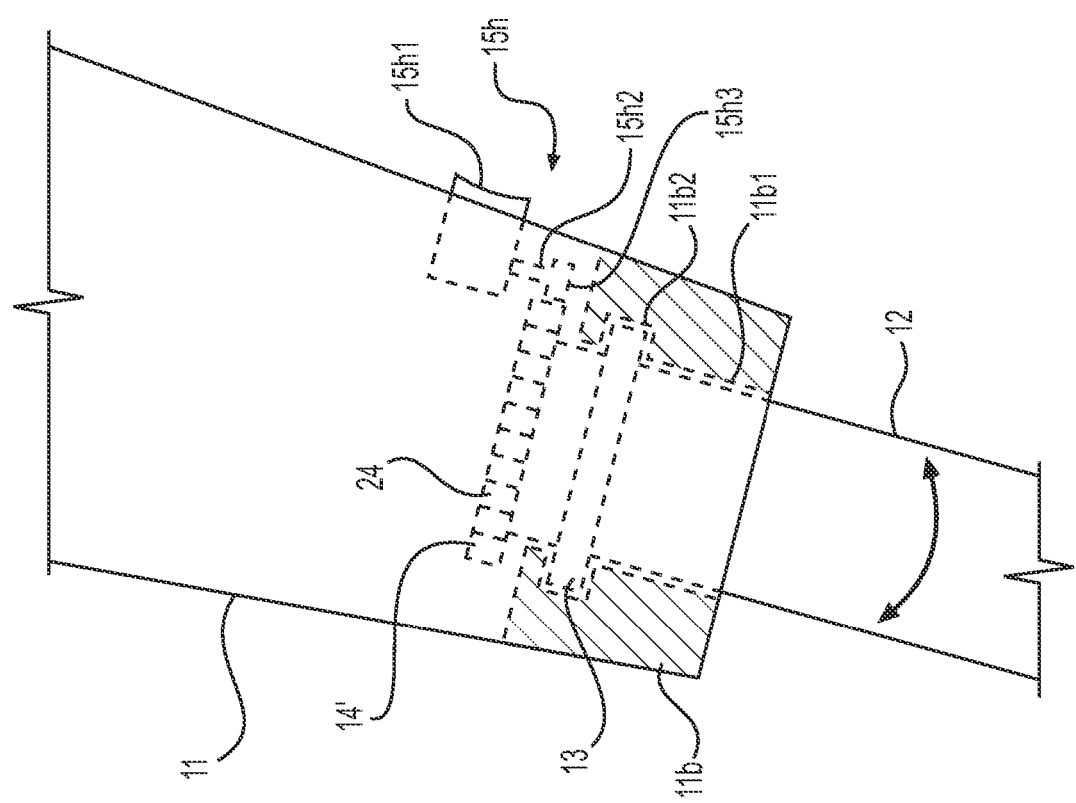

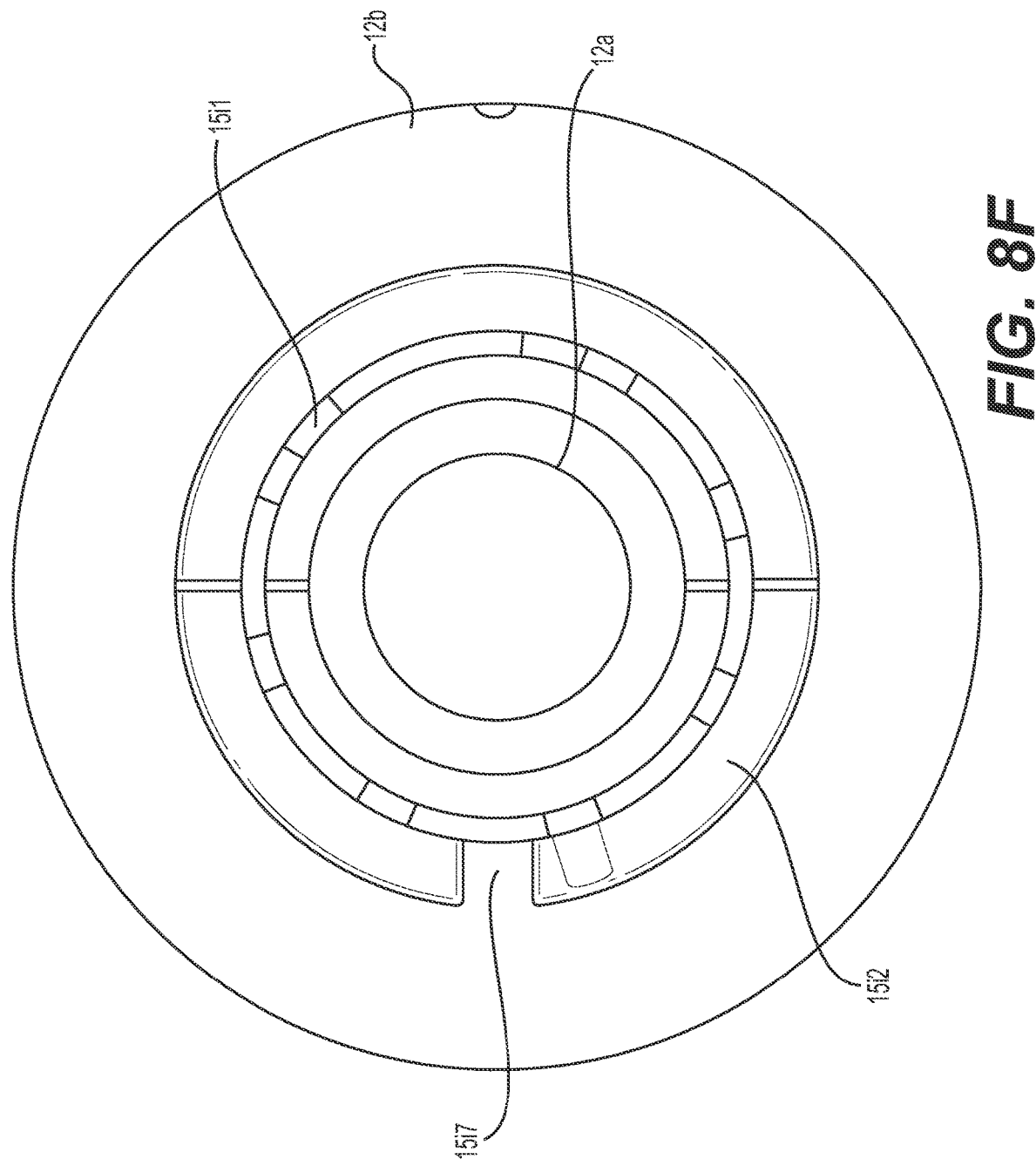

ROTATABLE MEDICAL DEVICE

CROSS-REFERENCE TO RELATED APPLICATIONS

This application claims the benefit of priority from U.S. Provisional Application No. 62/958,788, filed on Jan. 9, 2020, which is incorporated by reference herein in its entirety.

TECHNICAL FIELD

Embodiments of this disclosure relate generally to a medical device having a shaft that rotates relative to handle. More particularly, at least some embodiments of the disclosure relate to a medical device having a locking mechanism, which may be unlocked to allow for rotation of the medical device shaft or locked so that the shaft is stationary.

BACKGROUND

In certain medical procedures, physicians and/or technicians need to control a duodenoscope (or other scope or medical device) and other medical accessory devices. Depending on a patient's position relative to that of the physician's, the physician controlling the device may need to contort and/or twist their wrists and/or bodies so that the medical device is adjusted and positioned to face an intended target site. As a result, physicians may be at an increased risk to suffer ergonomic injuries to their hands, wrists, and back.

SUMMARY OF THE DISCLOSURE

According to an example, a medical device may comprise a shaft, a handle housing a proximal portion of the shaft, and a lock having a first configuration and a second configuration, wherein, in the first configuration of the lock, the shaft is rotatable about a longitudinal axis of the shaft relative to the handle, and, in the second configuration of the lock, the shaft is stationary relative to the handle.

In one example, the lock may further include a collar and a plurality of deflectors, wherein the plurality of deflectors surround a proximal portion of the shaft, wherein the collar surrounds the plurality of deflectors and the proximal portion of the shaft, and wherein a rotation of the collar in one direction places the lock into the first configuration, and the rotation of the collar in the opposite direction places the lock into the second configuration. In the first configuration the collar may be spaced apart from the plurality of deflectors allowing radial movement of the plurality of deflectors between the collar and the shaft, and in the second configuration the collar pushes the plurality of deflectors against the shaft so that the shaft is held stationary relative to the handle.

In another example, the lock may include a lever outside of the handle, a spring coupling a distal end of the lever to the handle, a tab connected to a proximal end of the lever, and a pivot point about which the lever pivots, wherein the tab is partially housed within the handle and is positioned to engage with one of a plurality of notches arranged about a periphery of the shaft. The lock may be defaulted into the second configuration, and the lock may be placed in a first configuration by depression of the distal end of the lever, thereby compressing the spring, and pivoting both the proximal end of the lever and the tab away from the handle so that the tab disengages with one of the plurality of notches.

In another example, the lock may include a pin, and a spindle housed within a spindle housing, wherein the spindle is spring-loaded, and both the spindle and the spindle housing are housed within the handle, wherein the pin is positioned to engage or disengage the spindle as the pin is advanced or retracted via depression of the pin, and wherein the spindle is positioned to engage or disengage with one of a plurality of notches arranged about a periphery of the shaft when the spindle is respectively radially advanced or retracted via engagement or disengagement with the pin. The lock may alternate between the first configuration and the second configuration via the depression of the pin. In the first configuration the spindle may be engaged with one of the plurality of notches, and in the second configuration the spindle may be disengaged with the one of the plurality of notches.

In another example, the lock may include a collar surrounding a portion of the shaft, wherein the collar includes a first flange, a second flange, and a pin driven through both the first flange and the second flange, wherein one end of the pin is coupled to a lock handle configured to rotate relative to the pin, and the other end of pin is coupled to a stop configured to prevent the pin from sliding out of both the first flange and the second flange. The lock may alternate between the first configuration and the second configuration via pivoting the lock handle. In the first configuration, the first flange and the second flange may be spaced apart by a gap, and in the second configuration, the first flange and the second flange may be in contact.

According to another example, the lock may include at least one spring coupled to a bearing, wherein one end of the spring is coupled to an inner wall of the handle and the other end of the spring is coupled to the bearing, and wherein the bearing is positioned to engage with one of a plurality of notches arranged about a periphery of the shaft via a spring force. The shaft may be rotated from the second configuration by an exertion of torsional forces greater than the spring force pressing the bearing against one of the plurality of notches.

In another example, the medical device may further comprise a motor, a cam coupled to the motor, and a switch configured to turn on/off the motor, wherein rotation of the cam by the motor engages the cam with one of a plurality of notches arranged about a periphery of the shaft.

In another example, the medical device may further comprise a housing configured to rotate with the shaft, wherein the housing houses a proximal portion of the shaft and is adjacent to the handle, and the housing includes a detent configured to engage with the lock. The lock may include a ring encompassing a proximal portion of the shaft. The ring may include a plurality of slots, each of which are configured to receive a portion of the detent, thereby anchoring the detent with the slots.

According to another example, a medical device may comprise a shaft including a distally-facing surface and a proximally-facing surface, a handle including a distally-facing surface and a proximally-facing surface, and a spring positioned between the proximally-facing surface of the shaft and the distally-facing surface of the handle, wherein in a compressed configuration of the spring, the shaft is rotatable about a longitudinal axis of the shaft relative to the handle, and in an extended configuration of the spring, the shaft is stationary relative to the handle. In the compressed configuration of the spring, the shaft may be pulled distally relative to the handle. The distally-facing surface of the handle may be a flange that juts radially outward relative to the handle, and the distally-facing surface of the handle may abut the proximally-facing surface of the shaft in the extended configuration of the spring.

According to another example, a method of positioning a shaft of a medical device may comprise inserting a distal end of a shaft of the medical device into the body of a subject, and after the insertion step, unlocking the handle from the shaft, rotating the shaft about a longitudinal axis of the shaft relative to the handle, and locking the handle to the shaft. The method may further comprise rotating the handle about a longitudinal axis of the handle relative to the shaft.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

FIGS. 3C-3F are perspective views of an exemplary lock of the medical device of FIG. 3A.

FIGS. 4A-4D are cross-sectional views of a portion of a medical device, according to other embodiments.

FIG. 6A is a perspective view of a portion of a medical device, according to another embodiment.

FIG. 6B is a sectional top view of a portion of the medical device of FIG. 6A.

FIG. 7A is a perspective view of a portion of a medical device, according to another embodiment.

FIG. 7B is a sectional top view of a portion of the medical device of FIG. 7A.

FIG. 8F is a top-sectional view of the medical device of FIG. 8A.

DETAILED DESCRIPTION

Reference will now be made in detail to aspects of the present disclosure, examples of which are illustrated in the accompanying drawings. Wherever possible, the same or similar reference numbers will be used through the drawings to refer to the same or like parts. The term "distal" refers to a portion farthest away from a user when introducing a device into a subject (e.g., patient). By contrast, the term "proximal" refers to a portion closest to the user when placing the device into the subject.

Both the foregoing general description and the following detailed description are exemplary and explanatory only and are not restrictive of the features, as claimed. As used herein, the terms "comprises," "comprising," "having," "including," or other variations thereof, are intended to cover a non-exclusive inclusion such that a process, method, article, or apparatus that comprises a list of elements does not include only those elements, but may include other elements not expressly listed or inherent to such a process, method, article, or apparatus. In this disclosure, relative terms, such as, for example, "about," "substantially," "generally," and "approximately" are used to indicate a possible variation of ±10% in a stated value or characteristic.

This disclosure may solve one or more of the limitations in the art. The scope of the disclosure, however, is defined by the attached claims and not the ability to solve a specific problem. The disclosure is drawn to medical devices including shafts, e.g., duodenoscopes, which may be rotatable. In embodiments, the shaft of such a medical device rotates relative to a handle of the medical device. Such rotation may depend on varying configurations of a lock included in the medical device. For example, such a lock may include a configuration in which the shaft may be freely rotatable relative to other portions of the medical device (including the handle), and another configuration in which the shaft remains stationary and is not rotatable relative to those other portions. Such medical devices may provide a user the option of rotating the shaft in-procedure, via any suitable manner, e.g., by hand, mechanically, electrically, etc., and an option of maintaining the shaft stationary in its current rotational position relative to a remainder of the device. Thus, a user of the device may comfortably access and view intended target sites, via rotation of the shaft, without having to twist and contort their wrists or other parts of the body, regardless of a patient's position relative to said user.

Figure 1A:
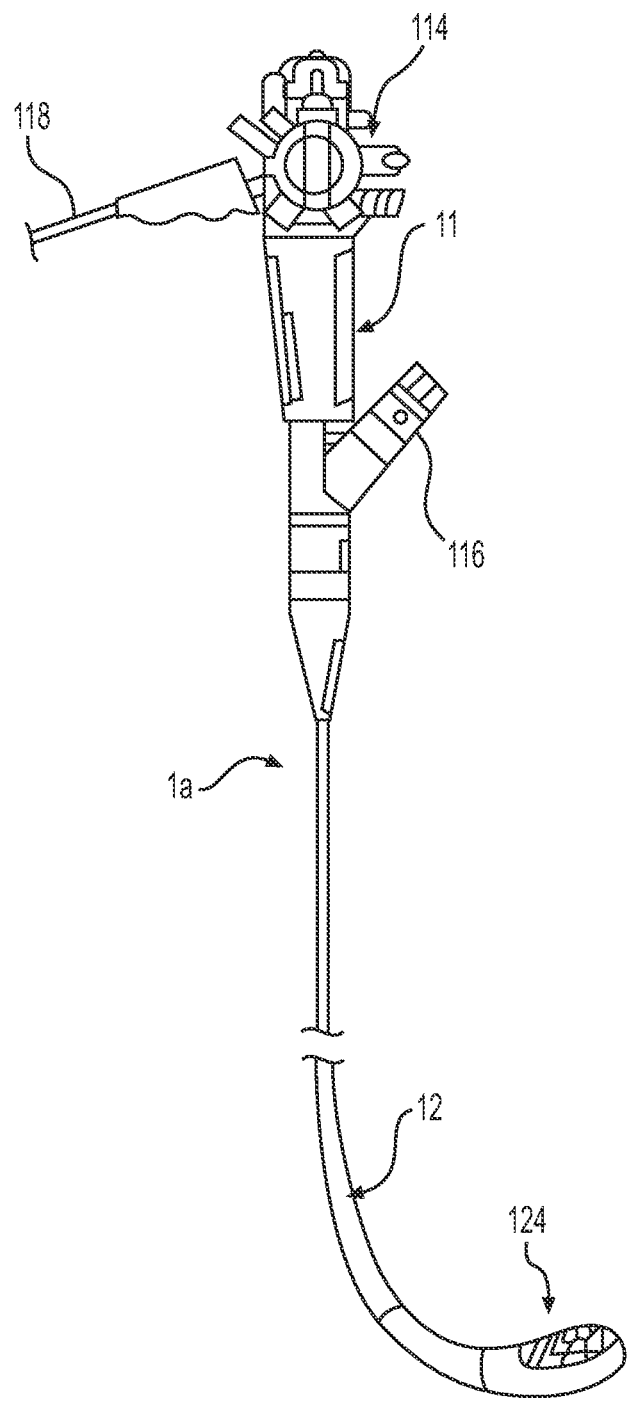
FIG. 1A is a perspective view of a medical device, according to an embodiment.

FIG. 1A shows a schematic depiction of an exemplary medical device 1a in accordance with an embodiment of this disclosure. Medical device 1a may be a duodenoscope, as shown, or any other like medical device, such as an endoscope, colonoscope, ureteroscope, bronchoscope, etc. or other medical device having a shaft and a handle. Medical device 1a may include a handle 11 and a shaft 12 coupled to a distal end of handle 11. Handle 11 of medical device 1a may have one or more lumens (not shown) that communicate with lumens of shaft 12. Handle 11 further includes an actuation mechanism 114, and at least one port 116 that opens into the one or more lumens of handle 11. At least one port 116 is sized and shaped to receive one or more instruments (not shown) therethrough, such as, for example, any suitable medical instrument of a medical system. For example, a medical instrument may include, but is not limited to, a guidewire, cutting or grasping forceps, a biopsy device, a snare loop, an injection needle, a cutting blade, scissors, a retractable basket, a retrieval device, an ablation and/or electrophysiology catheter, a stent placement device, a surgical stapling device, a balloon catheter, a laser-emitting device, and/or any other suitable instrument.

Handle 11 further includes a lock 15a that may be rotatable relative to the remainder of handle 11 and shaft 12, and the rotation of lock 15a may allow for the rotation of shaft 12 relative to handle 11 and vice versa. Rotatable lock 15a and its relationship with respect to handle 11 is described in further detail below.

Shaft 12 of medical device 11 may include a tube that is sufficiently flexible such that the shaft 12 is configured to selectively bend, rotate, and/or twist when being inserted into and/or through a patient's tortuous anatomy to a target treatment site. The treatment site may include a body lumen, including, for example any gastrointestinal lumen (esophagus, stomach, small and large intestines). Shaft 12 may have one or more lumens (not shown) extending therethrough that include, for example, a working lumen for receiving instruments. In other embodiments, shaft 12 may include additional lumens such as a control wire lumen for receiving one or more control wires, a fluid lumen for delivering a fluid, an illumination lumen for receiving at least a portion of an illumination assembly (not shown), and/or an imaging lumen for receiving at least a portion of an imaging assembly (not shown).

Still referring to FIG. 1A, an actuation mechanism 114 of medical device 1a is positioned on handle 11 and may include one or more knobs, buttons, levers, switches, and/or other suitable actuators. Actuation mechanism 114 is configured to control at least one of deflection of shaft 12 (including deflection of an articulation joint at a distal end of shaft 12 via actuation of one or more first control wires), actuation of a second control wire (e.g. for an elevator at the distal tip), delivery or removal of a fluid or other material, emission of illumination, and/or various imaging functions. The distal tip 124 of device 1a may include apparatus for lighting (e.g. LED) and imaging (e.g. a camera), an elevator to direct an instrument exiting the distal tip, and openings for irrigation and suction. A connector/cord 118 connects to a controller that may include processors and memory for controlling the various functions at the distal tip. A medical device 1a according to embodiments of the disclosure may include more or less structure and functionality than those described above.

Figure 1B:
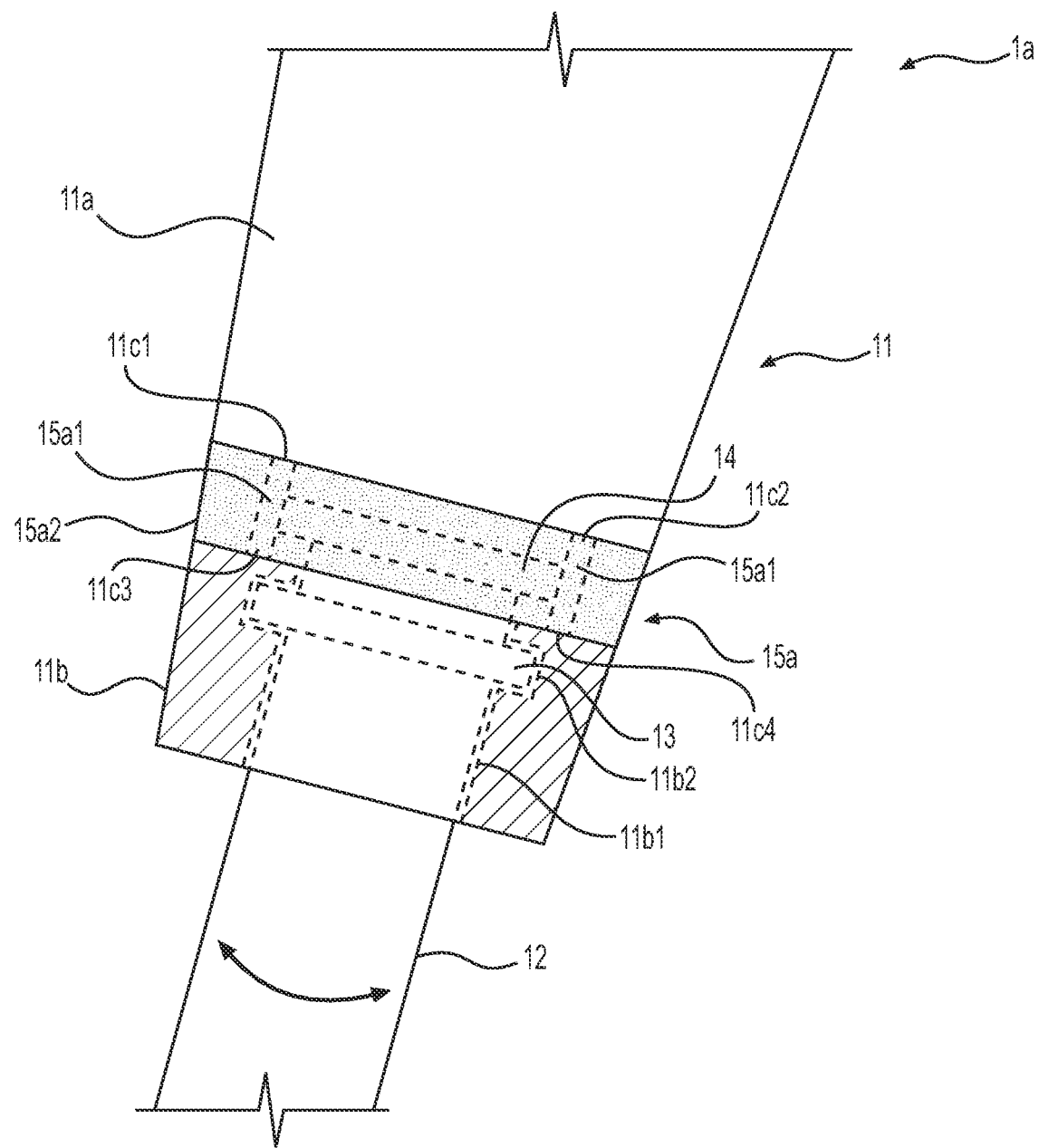
FIG. 1B is a perspective view of a portion of the medical device of FIG. 1A, according to an embodiment.
Figure 1C:
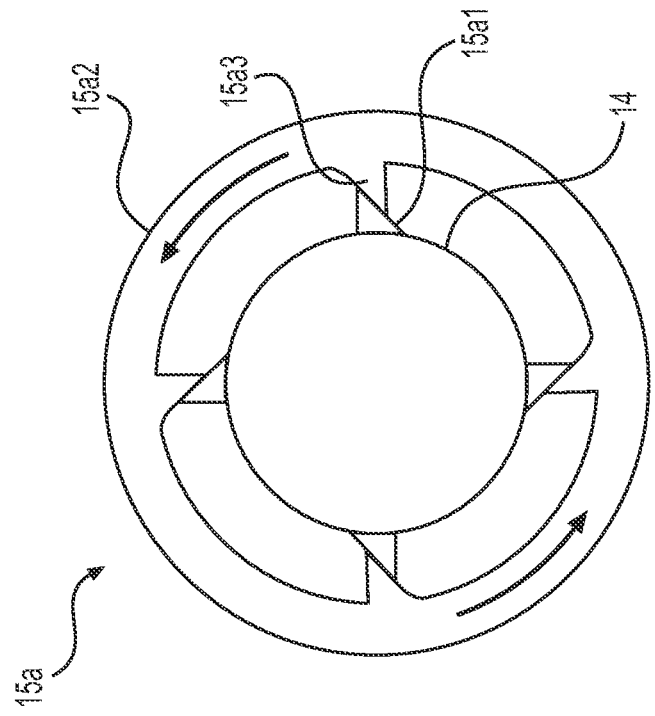
FIGS. 1C-1D are sectional top views of a portion of the medical device of FIG. 1A.
Figure 1D:
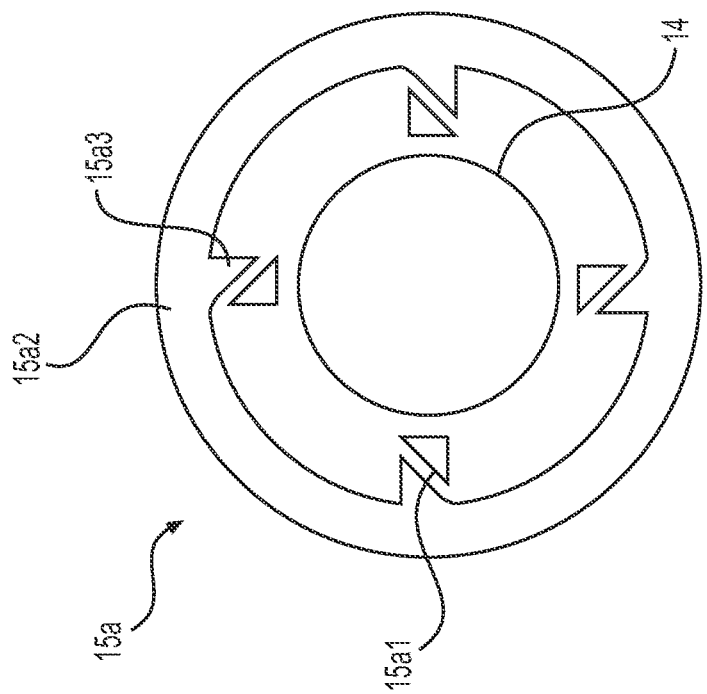

FIGS. 1B-1D illustrate an embodiment of a portion of medical device 1a in further detail. As shown, handle 11 houses a proximal portion of shaft 12. Handle 11 includes a lock 15a having a first configuration and a second configuration. In the first configuration of lock 15a, shaft 12 is rotatable about a longitudinal axis of shaft 12 relative to handle 11. In the second configuration of lock 15a, shaft 12 is fixed relative to handle 11.

Shaft 12, specifically a proximal portion thereof, includes a proximal flange 14 and a distal flange 13. As shown in FIGS. 1B-1D, proximal flange 14 is circular (see FIGS. 1C-1D showing top view) and is located at the proximal-most end of shaft 12. Alternatively, shaft 12 may extend further proximally, past proximal flange 14. Distal flange 13 is spaced distally from proximal flange 13 by a suitable distance. In some embodiments, distal flange 13 also has a circular cross-sectional shape. In some embodiments, the diameters of distal flange 13 and proximal flange 14 are the same. Between distal flange 13 and proximal flange 14 is a portion of shaft 12 having a smaller diameter than distal flange 13 and proximal flange 14. Portions of shaft 12 distal to distal flange 13 have a smaller diameter than that of distal flange 13, and may be of the same diameter as the portion of shaft 12 between distal flange 13 and proximal flange 14. In other embodiments, distal flange 13 and proximal flange 14 may have other suitable shapes and diameters.

Handle 11 has a proximal portion 11a and a distal portion 11b. Proximal portion 11a and distal portion 11b may be discrete components separated longitudinally by a space (which is occupied by lock 15a). Distal portion 11b houses a proximal portion of shaft 12. In particular, distal portion 11b includes an inner wall 11b1 defines a lumen that encompasses said proximal portion of shaft 12, so that minimal radial and longitudinal movement of said proximal shaft 12 is allowable. The lumen defined by inner wall 11b1 encompasses the portion of shaft 12 having a smaller diameter, and a groove 11b2 defined by inner wall 11b1 encompasses distal flange 13. As a result of inner wall 11b1 and groove 11b2 encompassing shaft 12, shaft 12 is inhibited from leaving distal portion 11b via the opening from which the remaining portion of shaft 12 exits handle 11. However, shaft 12 may be rotatable within distal portion 11b since inner wall 11b1 and groove 11b2 leave sufficient clearance from shaft 12 to allow for minimal radial movement and rotation of said shaft 12. It is also noted that handle 11 may be rotatable relative to shaft 12 via the same mechanism described herein.

Proximal portion 11a and distal portion 11b are connected together within the space between them by inner deflectors 15a1. Deflectors 15a1 extend longitudinally from proximal portion 11a to distal portion 11b. As shown in FIGS. 1C-1D, each deflector 15a1 may have a triangular cross-sectional shape. FIGS. 1C-1D show four deflectors evenly spaced around the circumference of proximal flange 14. However, the number of deflectors 15a1 is not particularly limited, and there may be more or less deflectors 15a1 in other medical device embodiments. Furthermore, the shape and the spacing/distribution of deflectors 15a1 are not particularly limited, and deflectors 15a1 may be of any suitable shape and/or distribution. Deflectors 15a1 are longitudinally rigid and flexible radially outward and inward. Each deflector 15a1 connects to proximal portion 11a at proximal connection points 11c1 and 11c2, and to distal portion 11b at distal connection points 11c3 and 11c4.

As previously noted, handle 11 includes lock 15a. Lock 15a includes a collar 15a2 and the aforementioned deflectors 15a1. Collar 15a2 sits in the space between proximal portion 11a and distal portion 11b of handle 11. Collar 15a2 is annular in shape, with an opening therein. Furthermore, collar 15a2 has a circular exterior shape, but is not limited thereto. A bottom end of proximal portion 11a may be of the same diameter as the adjacent surface, i.e., the top surface, of collar 15a2, and likewise, a top end of distal portion 11b may be of the same diameter as the adjacent surface, i.e., the bottom surface, of collar 15a2. Thus, distal portion 11b, collar 15a2, and proximal portion 11a may be sized in such a way that the radially outer surfaces of them are flush to one another. Collar 15a2 rotates about the longitudinal axis of handle 11 relative to proximal portion 11a and distal portion 11b. Collar 15a2 may be made of any suitable rigid material.

Collar 15a2 includes projections 15a3 that project radially inward from an inner circumferential surface of collar 15a2 toward the longitudinal axis of handle 11. As shown in FIGS. 1C-1D, each projection 15a3 may have a triangular cross-sectional shape. FIGS. 1C-1D show four projections evenly spaced around the inner circumferential surface of collar 15a2. However, the number of projections 15a3 is not particularly limited, as collar 15a2 may include more or less projections 15a3. Furthermore, projections 15a3 may be randomly spaced as desired. Regarding the shapes of projections 15a3, projections 15a3 may be of any shape configured to engage with deflectors 15a1. For example, FIGS. 1C-1D show projections 15a3 having surfaces that are complementary to the surfaces of deflectors 15a1, regardless of the rotational direction of collar 15a2.

The number of projections 15a3 may correspond to the number of deflectors 15a1, and such a number may dictate the rotational degree by which collar 15a2 may be rotated. For example, there are four projections 15a3 and four inner deflectors 15a1, as shown in FIGS. 1C-1D. Because both projections 15a3 and inner deflectors 15a1 are evenly arranged around the circumference of proximal flange 14, collar 15a2 may be rotatable 90° degrees clockwise or counter-clockwise to loosen or tighten lock 15a. In other embodiments, lock 15a may include six projections 15a3 and six inner deflectors 15a1, evenly distributed around proximal flange 14. In such embodiments, collar 15a2 may be rotatable 60° degrees clockwise or counter-clockwise to loosen or tighten lock 15a. Therefore, there may be any suitable number of projections 15a3 and inner deflectors 15a2, and the disclosure is not limited to the aforementioned examples.

FIG. 1C shows a top sectional view of proximal flange 14 and lock 15a in a loosened state/configuration. In this loosened configuration, collar 15a2 is in a loosened position relative to deflectors 15a1 and proximal flange 14. Specifically, collar 15a2 and its projections 15a3 are spaced apart, or disengaged, from inner deflectors 15a1, thereby allowing inner deflectors 15a1 to retain its natural, unbiased state within handle 11. In this configuration, no force is applied to deflectors 15a1 by projections 15a3, and shaft 12 is rotatable about a longitudinal axis of shaft 12 relative to handle 11 in this loosened configuration. Handle 11 may also be rotatable about a longitudinal axis of handle 11 relative to shaft 12 and collar 15a2.

Projections 15a3 are positioned relative to deflectors 15a1 so that counter-clockwise rotation of collar 15a2 would cause engagement between complementary surfaces of projections 15a3 and deflectors 15a1. Such engagement would cause deflectors 15a1 to flex radially inward toward proximal flange 14, due to a radially inward force component applied by projections 15a3 onto deflectors 15a1.

In contrast, FIG. 1D shows a top sectional view of proximal flange 14 and lock 15a in a tightened state/configuration. In this configuration, collar 15a2 has been rotated in a counter-clockwise direction so that projections 15a3 engage with and apply a force to deflectors 15a1. Due to said force, deflectors 15a1 are pressed/flexed radially inward toward the longitudinal axes of the handle and the shaft, so that deflectors 15a1 are, in turn, pushed against proximal shaft flange 14. Such engagement of deflectors 15a1 with proximal shaft flange 14 may provide sufficient friction force to keep shaft 12 stationary relative to handle 11. Said friction force may withstand typical procedural movement and adjustment of shaft 12, and prevent rotation thereof. In some embodiments, projections 15a3, deflectors 15a1, and/or proximal flange 14 may provide friction, e.g., be of any suitable frictious materials or comprise materials with roughened surfaces to enhance friction, so that friction forces resulting from their respective engagements help maintain the engagements until lock 15 is loosened. In other embodiments, any of the additional locks described in further detail below may be applied to medical device 1a to further inhibit shaft 12 from further rotation. To revert lock 15a from a tightened configuration to the described loosened configuration, collar 15a2 may be rotated in an opposite direction, e.g., a clockwise direction. Thus, lock 15a of medical device 1a may include a loosened configuration and a tightened configuration.

Referring to FIGS. 1A-1C, an example of how medical device 1a may be used is further discussed below. The distal end of shaft 12 of medical device 1a may be delivered into the body of a subject, adjacent to an intended target site. Imaging associated with medical device 1a, via any suitable image processing device, may assist in positioning of the distal end of shaft 12. Depending on the position of the subject and/or the intended target site relative to medical device 1a and/or a user of medical device 1a, the user may choose to rotate shaft 12 relative to handle 11. If lock 15a is in the previously described tightened configuration, the user may loosen collar 15a2 by rotating collar 15a2 in a clockwise direction. Such rotation disengages or separates projections 15a3 of collar 15a2 from inner deflectors 15a1 to place lock 15a in a loosened configuration. When lock 15a is in the loosened configuration, the user may rotate shaft 12 about a longitudinal axis of shaft 12 relative to handle 11, so that shaft 12 is better positioned relative to an intended target site and/or to allow the user to be in an ergonomic position. Alternatively, the user may rotate handle 11 relative to shaft 12 to allow the user's handling of handle 11 in a more ergonomic position, or for various other reasons. The user may rotate shaft 12 or handle 11, relative to the other, by any selected or predetermined degree. The user may then place lock 15 in a tightened configuration by rotating collar 15a2 in a counter-clockwise direction. Such rotation causes projections 15a3 to engage and press against deflectors 15a1 so that deflectors 15a1 flex radially inward toward proximal flange 14. The user may continue to tighten collar 15a2 via rotation thereof, until rotation of collar 15a2 is no longer possible and deflectors 15a1 are pressed against proximal flange 14. The manner in which collar 15a2 is rotated in a clockwise or a counter-clockwise direction is not particularly limited. As noted above, in some other embodiments, the user may actuate another suitable lock to ensure that shaft 12 is stationary relative to handle 11.

Figure 2:
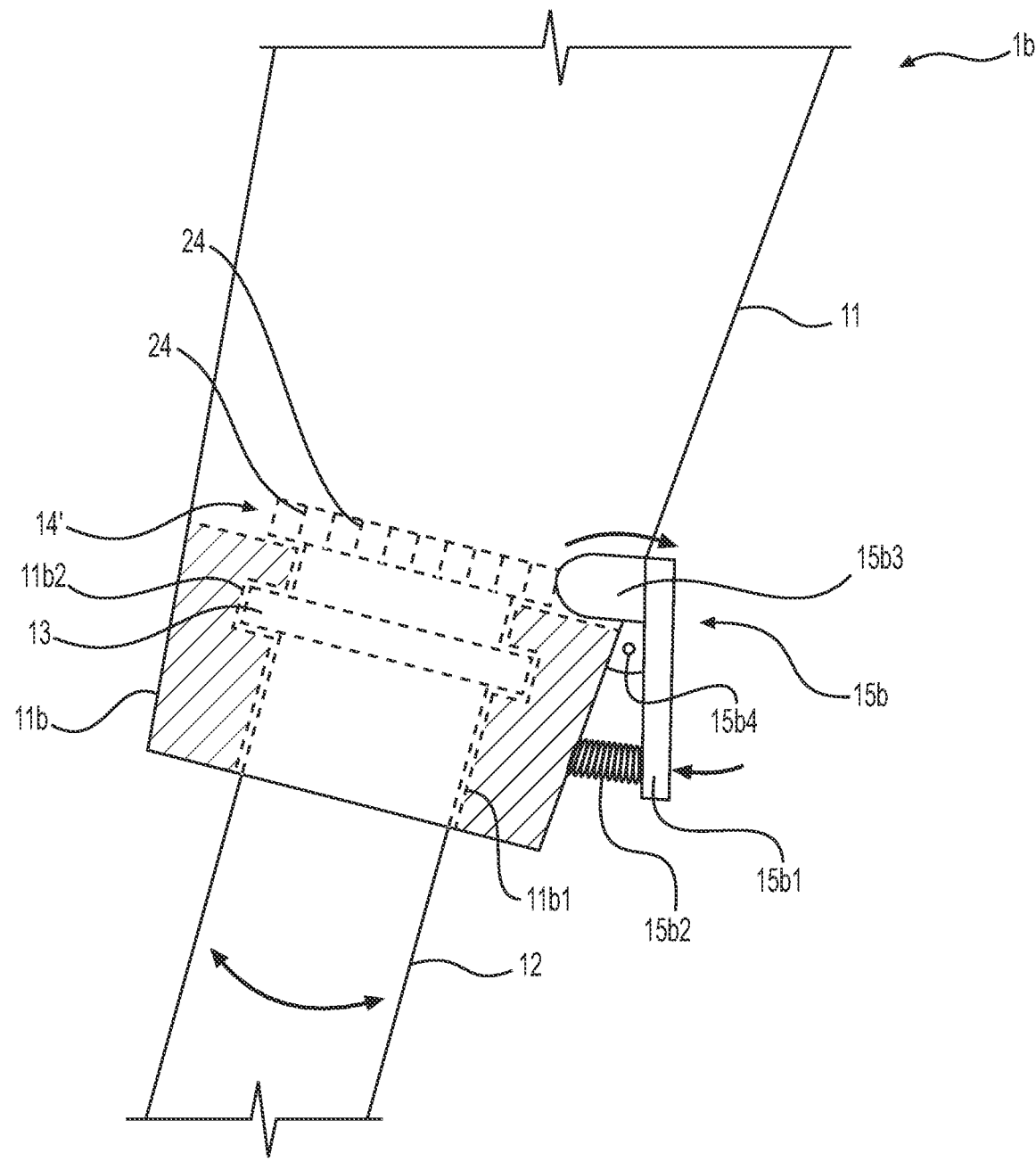
FIG. 2 is a perspective view of a portion of a medical device, according to another embodiment.

Medical device 1b, as shown in FIG. 2, is similar to device 1a in many respects. Like reference numerals refer to like parts. Differences between device 1a and device 1b will be described below. In device 1b, proximal flange 14' includes a plurality of notches 24 circumferentially arranged about an outer surface of proximal shaft flange 14'. Notches 24 may be depressions distributed on the outer circumferential surface of proximal shaft flange 14'. Notches 24 may be of a suitable depth to sufficiently catch or engage with a lock 15b to be described. While the number of notches 24 may not be particularly limited, it is noted that the number of notches corresponds to the number of rotational positions/degrees in which shaft 12 may be locked in place.

Lock 15b includes a lever 15b1, a spring 15b2, a tab 15b3, and a pivot 15b4. Lever 15b1 is not particularly limited in its shape and structure, so long as it is suitable for depression by a user. Lever 15b1 is positioned outside of handle 11. Spring 15b2 couples a distal end of lever 15b1 to an outer surface of handle 11. Spring 15b2 may have a sufficient spring force to withstand typical in-procedure manipulation of medical device 1b, but also allow for compression via a user applied force to lever 15b1. Tab 15b3 is connected to a proximal portion of lever 15b1 facing handle 11, and may partially enter or exit handle 11 via any suitable opening in handle 11. Tab 15b3 may enter or exit handle 11 to engage with or disengage from one of notches 24. It is noted that tab 15b3 may be of any suitable shape or size that may engage or catch one of notches 24. Pivot 15b4 couples the portion of lever 15b1 underneath tab 15b3 to the outer surface of handle 11. Therefore, pivot 15b4 allows lever 15b1, along with tab 15b3, to pivot about pivot 15b4, via compression or extension of spring 15b2.

In the default position of lock 15b, spring 15b2 is in full extension, thereby pushing the distal end of lever 15b1 outward via pivot 15b4. In this pivoted position, tab 15b3 engages with one of notches 24. Engagement may include the inward protruding tab 15b3 being caught in a depression of one of notches 24. Due to such engagement, shaft 12 remains stationary relative to handle 11 and is inhibited from any rotation in this locked configuration.

As indicated by the directional arrows shown in FIG. 2, depression of the distal end of lever 15b1 with sufficient force compresses spring 15b2, and pivots both the proximal end of lever 15b1 and tab 15b3 away from handle 11. The force to depress the distal end of lever 15b1 may be exerted by any suitable means, e.g., by hand, mechanically, or electrically. This causes tab 15b3 to disengage with one of notches 24. During disengagement, shaft 12 may be rotatable about a longitudinal axis of shaft 12 relative to handle 11, until lever 15b1 is released and lock 15b is reverted to its default locked configuration. Handle 11 may also be rotatable about a longitudinal axis of handle 11 relative to shaft 12 during disengagement. Because the locked configuration requires that tab 15b3 engages with one of notches 24, shaft 12 may be rotatable and lockable only in the plurality of rotational degrees/positions in which notches 24 and tab 15b3 align.

Medical device 1b may be used in a similar manner as medical device 1a, except a user may depress or release the distal end of lever 15b1 to unlock or lock the rotation of shaft 12 relative to handle 11, as opposed to tightening or loosening a collar. Furthermore, the user may rotate and lock shaft 12 in selected or predetermined rotational degrees in which one of notches 24 and tab 15b3 align.

Figure 3A:
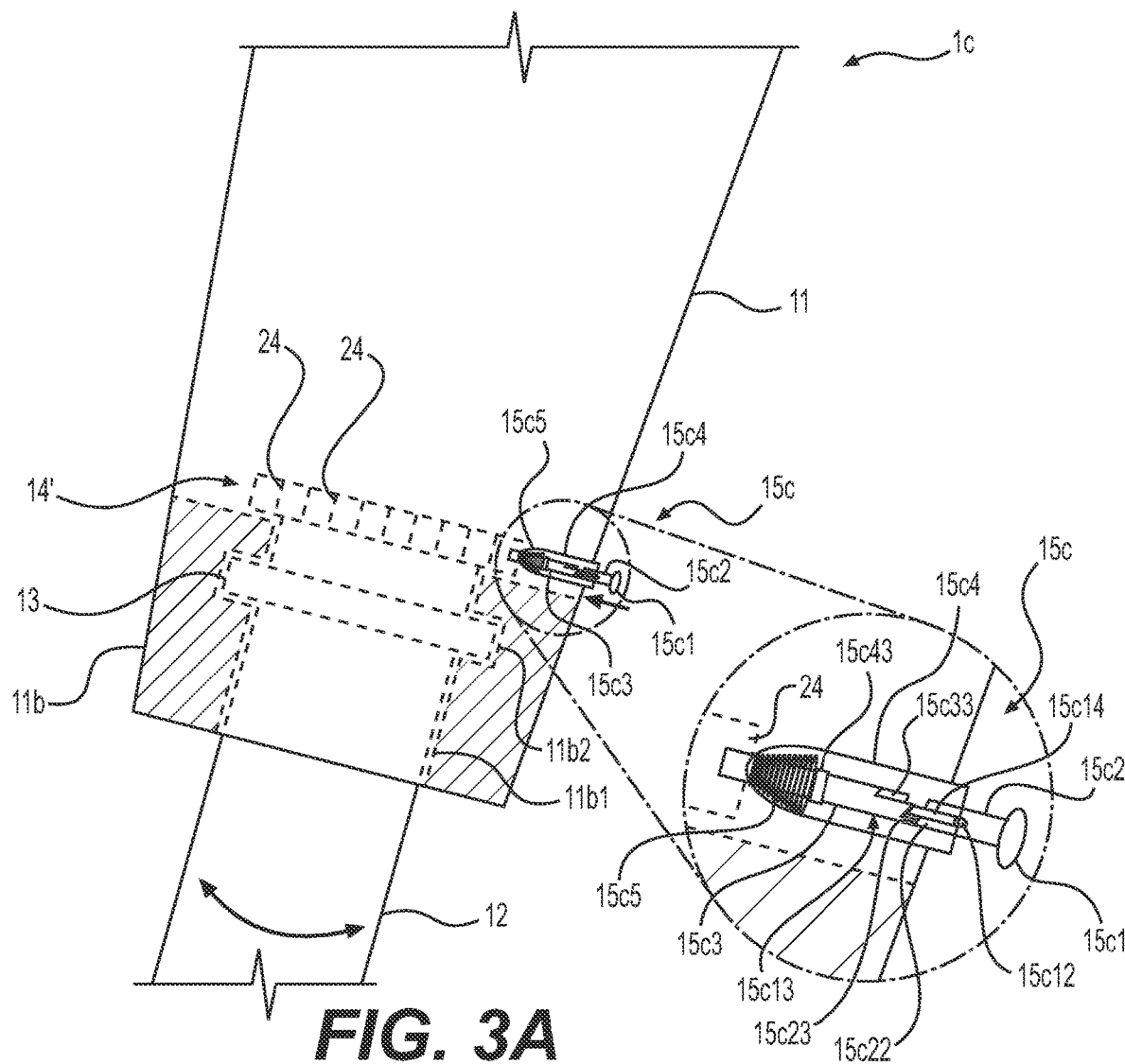
FIG. 3A is a perspective view of a portion of a medical device, according to another embodiment.
Figure 3B:
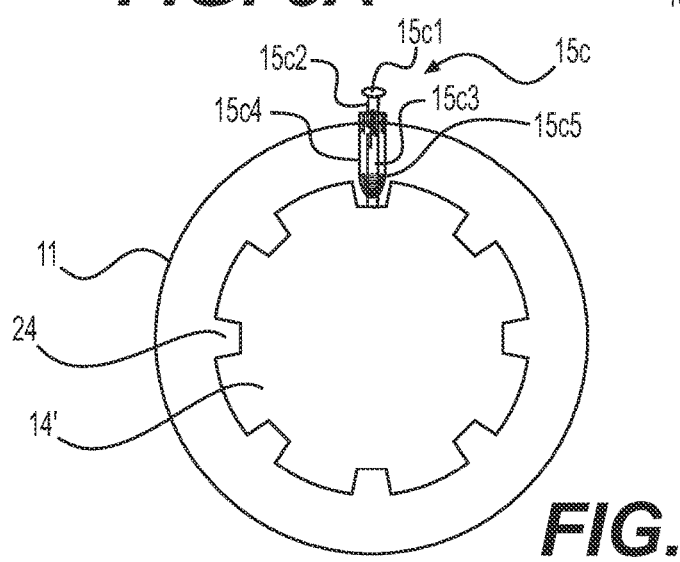
FIG. 3B is a sectional top view of a portion of the medical device of FIG. 3A.

Medical device 1c, as shown in FIGS. 3A-3B, is similar to device 1b in many respects. Like reference numerals refer to like parts. Differences between device 1b and device 1c will be described below. Lock 15c is a locking mechanism, which may be pressed inward and clicked to toggle between locked and unlocked configurations. Lock 15c includes a button 15c1 coupled to a pin 15c2, a spindle 15c3, a spindle housing 15c4, and a spring 15c5. Button 15c1 is positioned outside of handle 11. Button 15c1 is of any suitable size or shape so that a user may press or click button 15c1 towards handle 11. Pin 15c2, on one end, is coupled to the surface of button 15c1 facing handle 11. Pin 15c2 is configured to partially enter or exit handle 11 via a suitable opening on handle 11, as button 15c1 is pressed. Therefore, button 15c1 and pin 15c2 are configured so that as button 15c1 is pressed towards handle 11, pin 15c2 advances radially inward within handle 11. Pin 15c2, on the other end, includes a guide 15c12 running along the length of pin 15c2 (substantially parallel to an axis of pin 15c2), and a contact 15c22 adjacent to guide 15c12. Guide 15c12 is a slot that extends longitudinally from the end of pin 15c2 to about a midpoint of pin 15c2, but is not limited thereto in other examples. Guide 15c12 is open-ended at its end spaced from button 15c1 and may be of a dimension that is suitable to receive portions of spindle housing 15c4, as described in further detail below. The end surface of contact 15c22 is angled relative to (transverse to) an axis perpendicular to the longitudinal axis of pin 15c2, so that an angled edge is formed. Contact 15c22 may be of a length, width, and shape suitable to engage with portions of spindle 15c3, as described in further detail below. Pin 15c2 is not limited as described, and, in other embodiments, may be of any suitable size or shape for engaging with spindle 15c3 and spindle housing 15c4, and portions thereof.

Both spindle 15c3 and spindle housing 15c4 are supported and housed within handle 11 and are adjacent to proximal flange 14'. Spindle 15c3 is cylindrical in shape. Spindle 15c3 includes one end configured to engage with one of notches 24, a flange 15c43 that juts radially outward at around a mid-portion of spindle 15c3, and another end which includes a rotatable cam 15c13. Flange 15c43 is of a diameter greater than the remainder of spindle 15c3, but is less than that of spindle housing 15c4, so that spindle 15c3 may advance and retract linearly within housing 15c4. Rotatable cam 15c13 includes a plurality of teeth 15c23 and a plurality of channels 15c33 that are circumferentially distributed about rotatable cam 15c13. Specifically, the distribution is such that each pair of two adjacent teeth 15c23 have a channel 15c33 positioned between them, e.g., pair, channel, pair.

Teeth 15c23 have angled edges, and are specifically angled so that the edges of teeth 15c23 complement, e.g., are substantially parallel to, the edge of contact 15c22 as the two edges come into contact with one another. Furthermore, the space between adjacent teeth may accommodate contact 15c22. Channel 15c33 extends longitudinally from the cam-end of spindle 15c3 to a portion of spindle 15c3 that is prior to flange 15c43. Channel 15c33 is open-ended, and may be of a dimension that is suitable to receive portions of spindle housing 15c4, as described in further detail below.

Spindle housing 15c4 is tubular and is tapered inward on one end so that the tapered end contains spring 15c5. However, housing 15c4 is not limited thereto, and may be of any tubular shape that is open-ended on both ends. Housing 15c4 may be of any suitable dimensions to house spindle 15c3 and pin 15c2, and to allow for linear advancement or retraction of spindle 15c3 and pin 15c2 within housing 15c4. Housing 15c4 includes a support 15c14. Support 15c14 is a rail that protrudes inward from an inner surface of housing 15c4, and is configured to ride within guide 15c12 of pin 15c2 and channel 15c33 of spindle 15c3. Thus, support 15c14 may be of a extends that fits within both guide 15c12 and channel 15c33. Support 15c14 runs longitudinally from an end of housing 15c4 to a suitable distance towards the other end of housing 15c4. In some embodiments, the length of support 15c14 may be equal to or about the lengths of channel 15c33. The end of support 15c14, that is adjacent to spindle 15c3, includes an end that is angled to a degree equal to or about the same as that of contact 15c22. Thus, the angled edge of support 15c14, like contact 15c22, may complement, e.g., may be substantially parallel to, the angled surfaces of teeth 15c23 and may also be cradled within the space between adjacent teeth 15c23.

Spring 15c5 may wrap around an end portion of spindle 15c3 that is closest to notches 24. Furthermore, spring 15c5 may be positioned between an end of housing 15c4 and flange 15c43, thereby forming a spring-loaded spindle 15c3. As a result, spindle 15c3 may advance radially inward, via compression of spring 15c5, and retract radially outward, via release of spring 15c5. Spring 15c5 is not particularly limited, and may be any suitable spring.

Still referring to FIGS. 3A-3B, the relative positions of lock 15c components are further described below. Pin 15c2 is positioned, relative to spindle 15c3 and housing 15c4, so that pin 15c2 may engage spindle 15c3 as it advances radially inward within housing 15c4. Guide 15c12 of pin 15c2 rides along support 15c14 of housing 15c4 to advance or retract within housing 15c4. The engagement between pin 15c2 and spindle 15c3 causes spindle 15c3, in turn, to advance radially inward towards proximal flange 14'. Therefore, spindle 15$c$3 may be positioned so that spindle 15$c$3 may engage with one of notches 24 when spindle 15$c$3 advances radially inward. The distance between spindle 15$c$3 and proximal flange 14' may be so that spindle 15$c$3 engages with notches 24 when spindle 15$c$3 is fully extended inwards, but spindle 15$c$3 does not engage with notches 24 when spindle 15$c$3 is retracted back towards housing 15$c$4. Moreover, the distance between housing 15$c$4 and proximal flange 14' may be so that housing 15$c$4 does not get caught in one of notches 24.

Referring to FIGS. 3C-3F, the unlocked and locked configurations of lock 15$c$ are further described. In the unlocked configuration, both pin 15$c$2 and spindle 15$c$3 are fully retracted. In this retracted position, contact 15$c$22 is cradled in the space between adjacent teeth 15$c$23, and support 15$c$14 is within channel 15$c$33 (see FIG. 3C). As button 15$c$1 (not shown in FIGS. 3C-3F) is pressed or clicked by any suitable force, contact 15$c$22 presses against one of teeth 15$c$23 of cam 15$c$13, thereby compressing spring 15$c$5 (not shown) and extending spindle 15$c$3 radially inward so that support 15$c$14 is out of channel 15$c$33 (see FIG. 3D). Because support 15$c$14 is no longer anchored within channel 15$c$33, and the spring force of spring 15$c$5 presses contact 15$c$22 and cam 15$c$13 against one another, the angled edges of contact 15$c$22 and support 15$c$14 ride along one of teeth 15$c$23, thereby initiating rotation of cam 15$c$13 so that adjacent teeth 15$c$23 cradle both support 15$c$14 and contact 15$c$22 (see FIG. 3E). As button 15$c$1 is released, pin 15$c$2 retracts by an extent so that contact 15$c$22 is out of the space between adjacent teeth 15$c$23, thereby further rotating cam 15$c$3 so that support 15$c$14 is solely anchored between adjacent teeth 15$c$23 and contact 15$c$22 rests above one of teeth 15$c$23 (see FIG. 3F). This prevents rotated spindle 15$c$3 from returning to its original, retracted position. Thus, as shown in FIG. 3F, spindle 15$c$3 is extended relative to its original position (shown in FIG. 3C), and is extended to an extent such that spindle 15$c$3 engages with one of notches 24 of proximal flange 14' (not shown). Such engagement between spindle 15$c$3 and one of notches 24, inhibits shaft 12 from being rotated and maintains shaft 12 in a stationary position. Thus, this position of lock 15$c$ may be described as the locked configuration.

By pressing or "clicking" button 15$c$1 again, pin 15$c$2 again engages spring-loaded spindle 15$c$3 and cam 15$c$13, such that spindle 15$c$3 again extends and rotates simultaneously within housing 15$c$4. Upon release of button 15$c$1, cam 15$c$13 rotates so that support 15$c$14 of housing 15$c$4 falls within channel 15$c$33 of cam 15$c$13 so that, spring 15$c$5 extends to its default state, and spindle 15$c$3 returns to its original, retracted position (shown in FIG. 3C). In this state, spindle 15$c$3 is retracted to an extent so that spindle 15$c$3 is disengaged from one of notches 24, and lock 15$c$ is reverted to an unlocked configuration.

Repeated toggling of clickable button 15$c$1 will alternate lock 15$c$ between the aforementioned unlocked and locked configurations. It is noted that if spring-loaded spindle 15$c$3 fails to engage with one of notches 24, additional rotation of shaft 12 may be necessary so that spindle 15$c$3 may engage with any one of notches 24 and place lock 15$c$ in a locked configuration. Thus, medical device 1$c$ may be used in the same manner as medical device 1$b$, except a user may depress or "click" button 15$c$1 to unlock or lock the rotation of shaft 12, as opposed to depressing and releasing a lever. Furthermore, the user may rotate and lock shaft 12 in selected or predetermined rotational degrees in which one of notches 24 and spindle 15$c$3 align.

Referring to FIGS. 4A-4B, another embodiment of medical device 1$d$1 is described below. Similar to previously described medical device embodiments, medical device 1$d$1 includes a handle 11' and a shaft 12'. Handle 11', specifically a distal portion thereof, includes a distally-facing surface, e.g., proximal flange 21$a$, and a proximally-facing surface, e.g., distal flange 21$b$. Distal flange 21$b$ is spaced distally from proximal flange 21$a$ by a suitable distance. Furthermore, proximal flange 21$a$ and distal flange 21$b$ jut radially outwards and are both circular in cross-sectional shape. Distal flange 21$b$ is of a smaller diameter than proximal flange 21$a$. However, both distal flange 21$b$ and proximal flange 21$a$ are of diameters greater than the portion of handle 11' between flanges 21$a$, 21$b$ and other remaining portions of handle 11'.

Shaft 12' also includes a proximally-facing surface, e.g., handle 15$d$1 and a distally-facing surface, e.g., flange 15$d$2. Shaft handle 15$d$1 encompasses at least a proximal portion of shaft 12'. Shaft handle 15$d$1 has a diameter greater than that of more distal portion of shaft 12', as handle 15$d$1 juts radially outward relative to those more distal portions and tapers in a distal direction. A proximal portion of handle 15$d$1 has a diameter that is the same as the diameter of proximal flange 21$a$ of handle 11'. The proximal end of shaft handle 15$d$1 includes flange 15$d$2.

Shaft flange 15$d$2 is annular in shape and juts radially inward. Annular shaft flange 15$d$2 includes an opening that receives a distal portion of handle 11'. Specifically, said opening is of a diameter that sufficiently encompasses the portion of handle 11' between the proximal flange 21$a$ and distal flange 21$b$. Shaft flange 15$d$2 juts radially inward by a distance such that the proximal end of shaft handle 15$d$1 may be flush with proximal flange 21$a$ while also allowing for minimal radial movement of handle 11' within shaft handle 15$d$.

A spring 15$d$3 is positioned between shaft flange 15$d$2 and distal handle flange 21$b$. Spring 15$d$3 may be any suitable spring, and is not particularly limited. Spring 15$d$3 may have a spring force sufficiently greater than other forces associated with typical in-procedure manipulation of medical device 1$d$. Spring 15$d$3 is positioned so that it is parallel to the longitudinal axis of handle 11'. As a result of such configuration, shaft flange 15$d$2 abuts proximal handle flange 21$a$, and distal handle flange 21$b$ abuts shaft 12', when spring 15$d$3 is in its default, extended position. FIG. 4A shows the default configuration of medical device 1$d$. In this default state, spring 15$d$3 pushes shaft flange 15$d$2 against proximal handle flange 21$a$, and distal flange 21$b$ against shaft 12', thereby interlocking shaft 12' with handle 11'. Furthermore, abutting surfaces of shaft flange 15$d$2 and proximal flange 21$a$, and of flange 21$b$ and shaft 12', may provide friction, e.g., be of frictious materials or comprise materials with roughened surfaces to enhance friction, further enhancing the interlocking of shaft 12' with handle 11'. Thus, in its default interlocked configuration, lock 15$d$ inhibits shaft 12' from being rotated relative to handle 11' and maintains shaft 12' in a stationary position.

FIG. 4B shows an unlocked configuration of medical device 1$d$1. Medical device 1$d$1 is placed into this configuration when shaft 12' is pulled distally relative to handle 11' or handle 11' is pulled proximally relative to shaft 12' by any suitable manner. This results in spring 15$d$3 compressing, thereby disengaging, e.g., separating, shaft flange 15$d$2 from proximal handle flange 21$a$, and flange 21$b$ from shaft 12'. As a result of such disengagement, shaft 12' may be rotatable about a longitudinal axis of shaft 12 relative to handle 11 while in this unlocked configuration. Handle 11' may also be rotatable about a longitudinal axis of handle 11' relative to shaft 12'. It is noted that the force necessary to actuate said disengagement must be greater than forces typically generated by in-procedure manipulation of shaft 12'. To revert medical device 1d back to its default interlocked state, shaft 12' may be released from any pulling forces so that spring 15d3 may naturally extend, and again, push shaft flange 15d2 against proximal handle flange 21a, and flange 21b against shaft 12'.

In additional embodiments, the outer surfaces of shaft handle 15d1 may be of a frictious or roughened material to assist a user in gripping handle 15d1, and pulling or pushing shaft 12'. Medical device 1d1 may be used in the same manner as medical device 1a, except a user may pull shaft 12' distally to unlock or interlock the rotation of shaft 12, as opposed to tightening or loosening a collar.

FIGS. 4C-4D show an alternative embodiment of medical device 1d2 that is similar in structure and operation as medical device 1d1. The differences between device 1d2 and device 1d1, illustrated in FIGS. 4A-4B, are further detailed below.

In FIGS. 4C-4D, handle 11" includes proximal flange 21a and distal flange 21b. Both proximal flange 21a and distal flange 21b jut radially inwards and are annular in shape. Annular distal flange 21b has an opening configured to receive a proximal portion of shaft 12". Said opening has a diameter sufficient to encompass a proximal portion 15b1 of shaft 12", while also allowing for minimal radial movement of shaft 12", within the opening. Shaft 12" includes shaft flange 15d2 at its proximal end. Shaft flange 15d2 juts radially outward and is circular in shape. Thus, shaft flange 15d2 has a diameter greater than the remaining portions of shaft 12". The outer diameter of shaft flange 15d2 is greater than the inner diameter of both proximal flange 21a, and distal flange 21b, such that shaft flange 15d2 is secured between proximal flange 21a and distal flange 21b of handle 11". The outer diameter of shaft flange 15d2 is slightly less than the inner diameter of portions of handle 11" between flanges 21a, 21b, allowing for minimal radial movement of shaft 12" within handle 11". Spring 15d3 may be the same, and may be positioned in the same manner, as in previously described device 1d1. As a result, spring 15d3 forces shaft flange 15d2 against proximal flange 21a, and with their frictious surfaces, fixes shaft 12" to handle 11". Thus, medical device 1d2 may be alternated between the default interlocked configuration and the unlocked configuration in the same manner and mechanism as that of medical device 1d1.

In some other embodiments, springs 15d3 may be positioned so that they push handle 11" and shaft 12" away from each other. Thus, a force pushing shaft 12" proximally towards handle 11" may be applied to disengage shaft 12" from handle 11", and allow for rotation of shaft 12". In other embodiments, lock 15d may further include a locking ring to ensure that shaft flange 15d2 and the handle flanges do not disengage in-procedure. The locking ring is not particularly limited, and may be any mechanism or component that inhibits shaft 12' from pulling away from handle 11', and vice versa, e.g., a compression fit ring. In other embodiments, lock 15d may include a longitudinal locking mechanism, instead of a radial, locking ring. In one example, a longitudinal locking mechanism may engage and disengage with the handle or shaft being pulled or pushed apart, to separate locking interfaces (e.g. 15d1 or 21b and 15d2 or 21a in FIGS. 4A-4B, and 15d2 or 21a in FIGS. 4C-4D). Locking interfaces may include a square notch or a square notch with a rounded top to guide the locking interfaces during engagement.

Figure 4F:
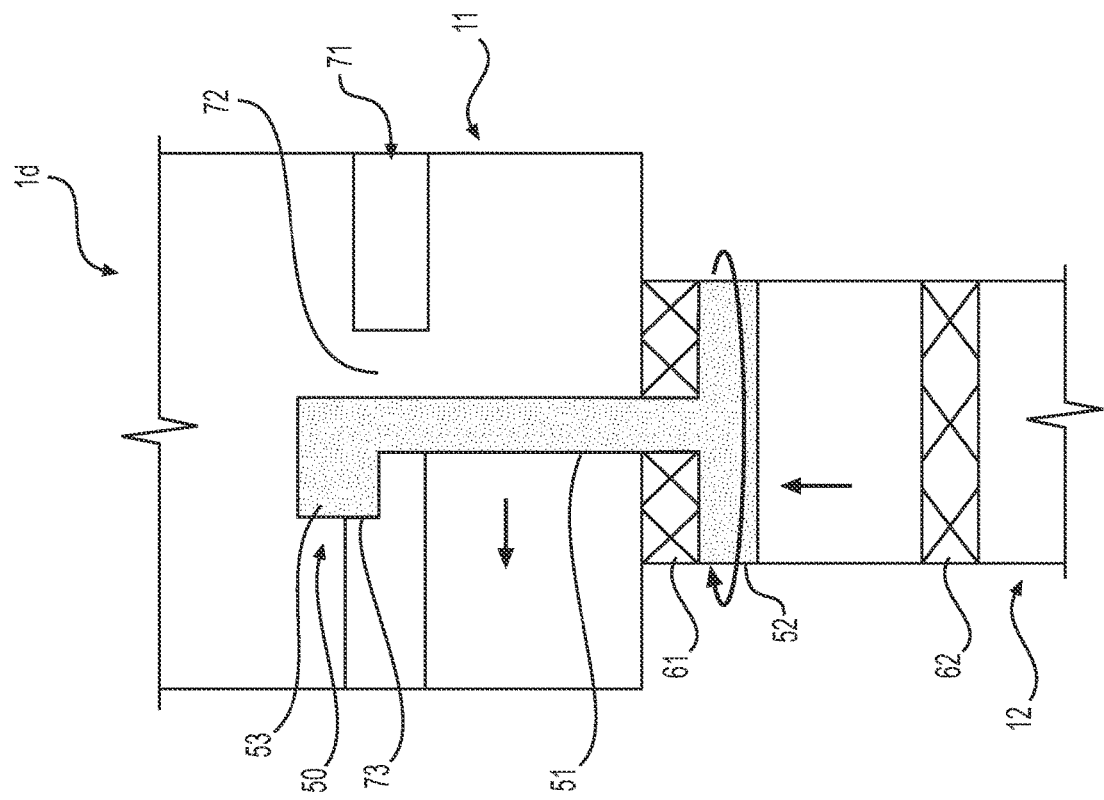
FIGS. 4E-4F are side views of a portion of a medical device including an example of a longitudinal lock, according to an embodiment.
Figure 4E:
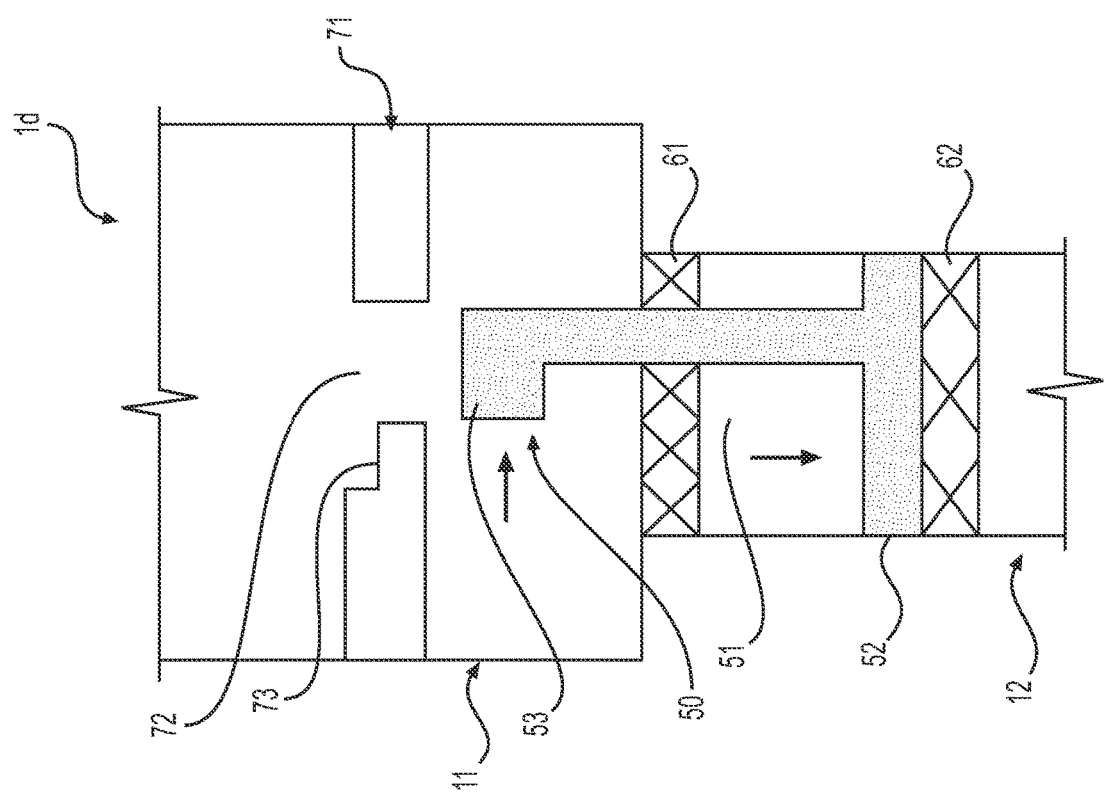

Referring to FIGS. 4E and 4F, a device including another example of a longitudinal locking mechanism is further described below. Device 1d may be similar to devices 1d1 and 1d2 described above. Handle 11 and shaft 12 of device 1d may be interlocked in the same or a similar manner as devices 1d1 and 1d2. Thus, shaft 12 may also be pulled distally to unlock itself from an interlocked state, and to rotate about a longitudinal axis of shaft 12 relative to handle 11. To ensure undesired unlocking/disengagement from the interlocked state, device 1d includes longitudinal lock 50, handle ring 71, a first shaft ring 61, and a second shaft ring 62.

Lock 50 is a single piece (though it could be multiple connected pieces) that is fitted within and/or around a proximal portion of shaft 12. Lock 50 includes a base ring 52, a longitudinal body 51, and a head 53. Ring 52 may be the portion of lock 50 that is fitted around shaft 12. The diameter of the space within ring 52 may be such that ring 52 may rotate and/or slide linearly while fitted around shaft 12, relative to device 1d. The diameter of base ring 52 may be any suitable diameter to allow for longitudinal body 51 to extend towards handle ring 71, without being impeded by the proximal facing surfaces of handle 11. To avoid such impedance, in some embodiments, ring 52 may be fitted around a shaft handle that is flush against handle 11, such as the proximal portion of shaft handle 15d1 of FIGS. 4A-4B. Longitudinal body 51 may be fixed to an outer edge or circumference of ring 52. Body 51 extends proximally towards handle ring 71. The shape of body 51 may be any suitable shape, e.g., linear, curved radially outwards, etc., to allow for body 71 to extend proximally over outer surfaces of handle 11. In some exemplary embodiments, body 51 may be formed such that the distal end (attached to ring 52) is closer to the central axis of the shaft than head 53, which is relatively farther away from the central axis of the shaft. Thus, the shape of body 51 may be tuned to avoid interference with the distal end of the handle as a user rotates between the locked and unlocked states. Alternatively, body 51 may maintain a distance from the central axis and handle 11 may have a cutout to accommodate body 51, as it rotates between the locked and unlocked positions. Body 51 may be of any suitable length that is sufficient to allow head 53 to reach and engage with ring 71. Body 51 may be of any suitable material that can withstand typical in-procedure pulling forces against shaft 12. Moreover, body 51 may be positioned on ring 52 so that it may be received within a gap 72 of handle ring 71 (further described below). Head 53 may be of any suitable shape or size to pass through gap 72 of ring 71. Moreover, head 53 may protrude in a direction towards a recess 73 of ring 71, and may protrude by a suitable length so that it may rest and remain on recess 73.

Handle ring 71 may be fixed around all or a portion of an outer surface of handle 11. Ring 71 may include a break along the circumference of ring 71, thereby forming a gap 72. Gap 72 may be of any suitable width that allows for head 53 and body 51 of ring 52 to pass through. The end of ring 71 facing head 53 may further include recess 73, noted above. Recess 73 may be a depression on the aforementioned end of ring 71 that accommodates for head 53 to anchor against. First shaft ring 61 and second shaft ring 62 may be fixed onto shaft 12. Rings 61 and 62 may be positioned along a proximal portion of shaft 12. Rings 61 and 62 may respectively be positioned proximal and distal of ring 52, thereby defining a space within which ring 52 may slide linearly. The defined space may be of a distance in accordance with the distance needed for head 53 to pass through gap 72 and reach recess 73. Ring 61 may also serve the function as a catch/stop against ring 52, thereby inhibiting shaft 12 from being pulled distally away from handle 11.

In view of the above, lock 50 may have two states, an unlocked state (as shown in FIG. 4E) and a locked state (as shown in FIG. 4F). In the unlocked state, ring 52 may rest against second shaft ring 62, and thus, head 53 may be distal of gap 72. In this state, shaft 12 may be pulled distally to unlock itself from an interlocked state, and to rotate about a longitudinal axis of shaft 12 relative to handle 11. To transition lock 50 into a locked state, ring 52 may be slid/translated linearly in a proximal direction, so that head 53 and a proximal portion of body 51 may pass through gap 72. To reach a sufficient distance at which head 53 may engage with recess 73, ring 52 may be slid linearly until it abuts first shaft ring 61. Ring 52 may then be rotated, as indicated by the directional arrows, so that head 53 meets and rests on recess 73, thereby anchoring lock 50 to handle ring 71. As a result, shaft 12 may be inhibited from being pulled distally away from handle 11. Thus, lock 50 may transition between an unlocked state and a locked state, as the user desires.

Figure 5A:
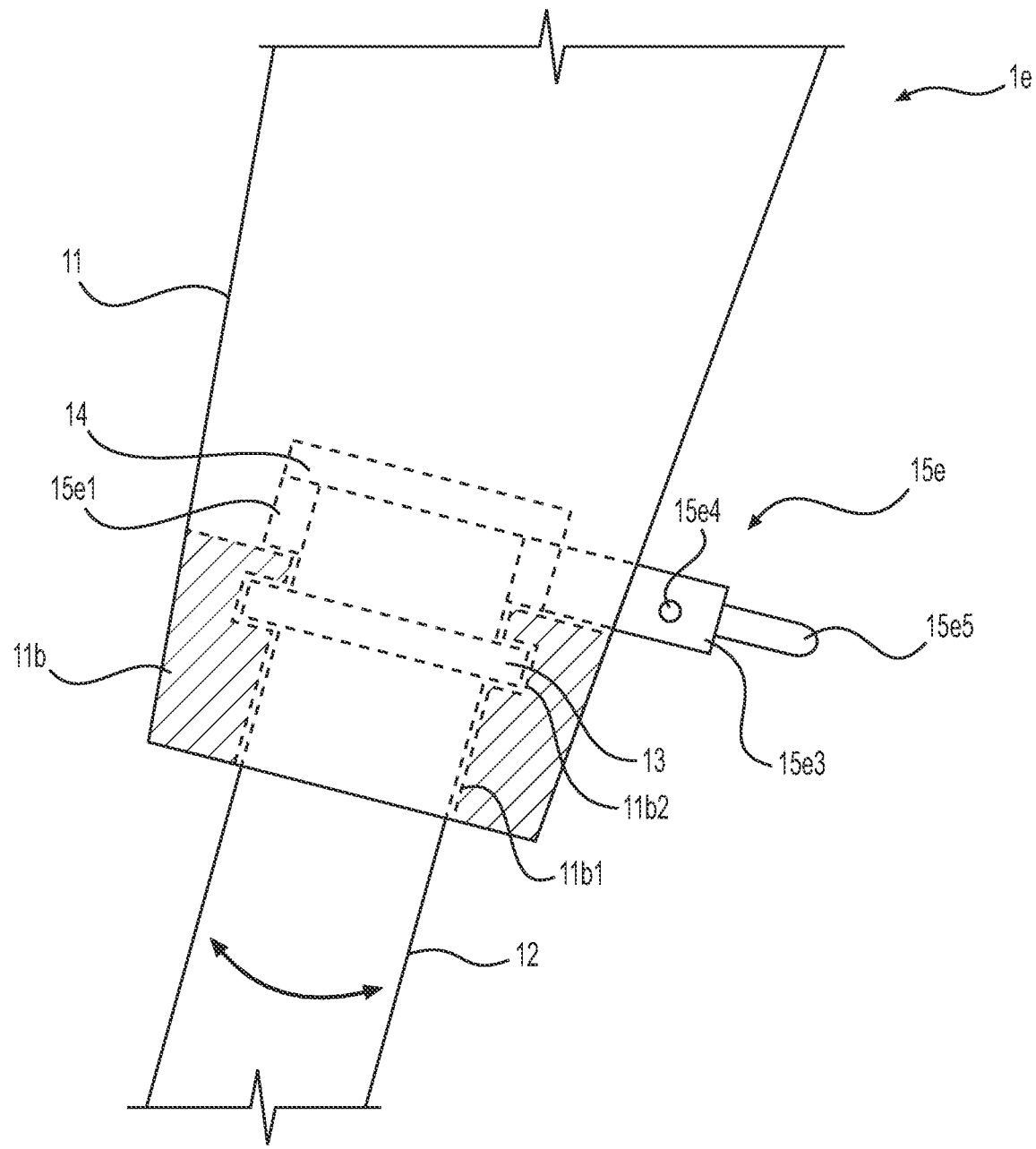
FIG. 5A is a perspective view of a portion of a medical device, according to another embodiment.
Figure 5C:
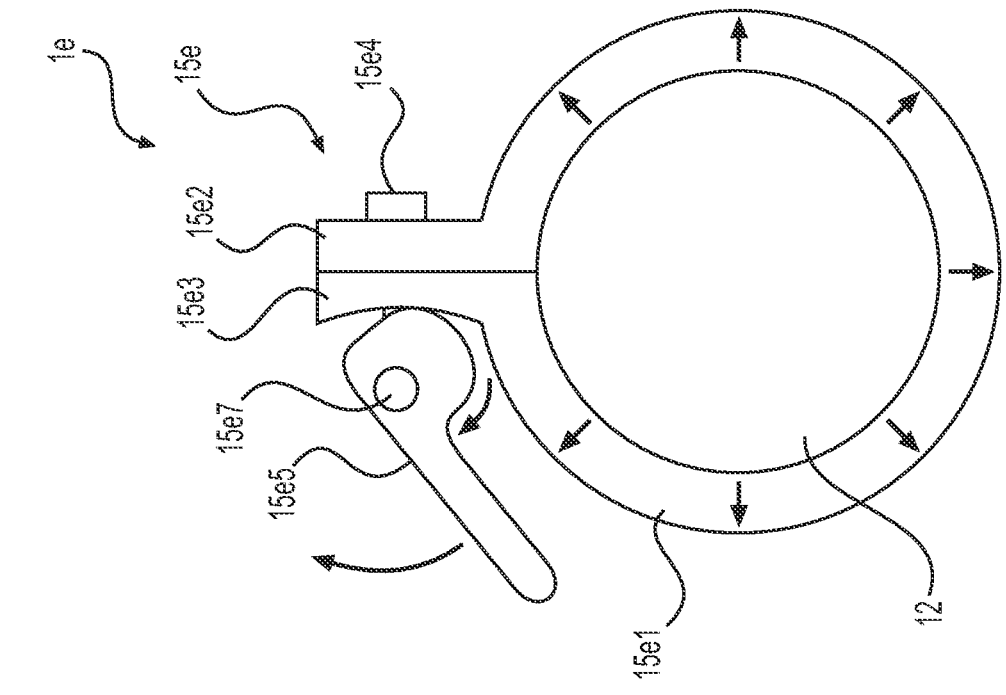
FIGS. 5B-5C are sectional top views of a portion of the medical device of FIG. 5A.
Figure 5B:
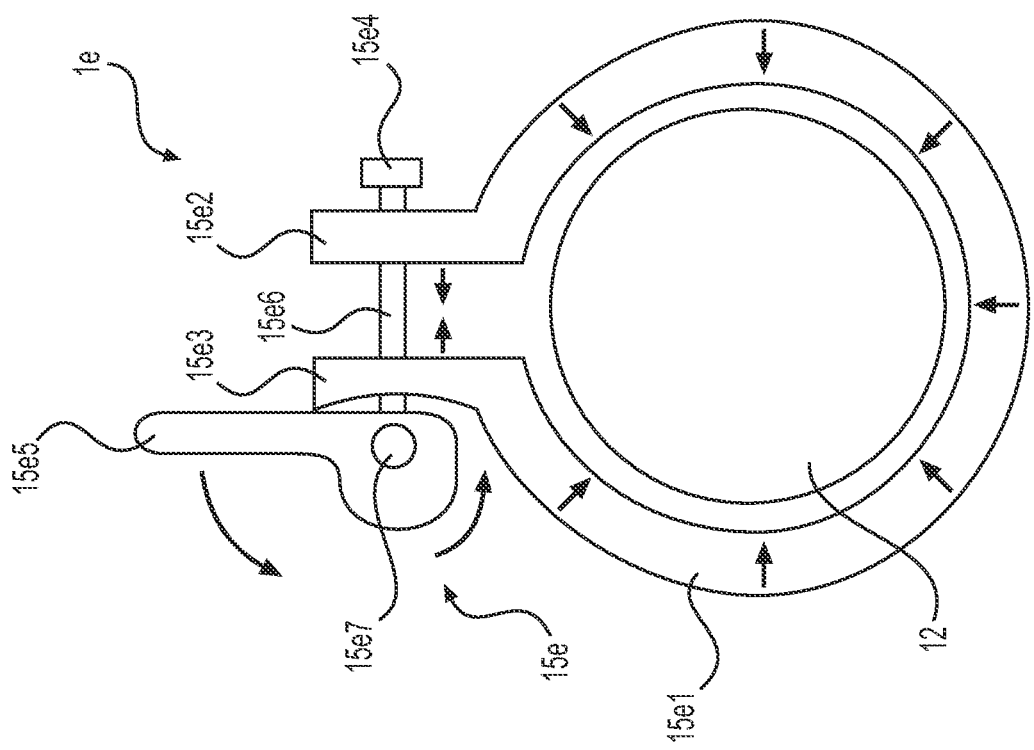

Medical device 1e, as shown in FIGS. 5A-5C, is similar to device 1a in many respects. Like reference numerals refer to like parts. Differences between device 1a and 1e will be described below. Handle 11 includes lock 15e. Lock 15e includes a collar 15e1 surrounding a portion of shaft 12 between distal flange 13 and proximal flange 14. Specifically, collar 15e1 is positioned between inner wall 11b1 and proximal flange 14. Collar 15e1 may be of any suitable flexible material, e.g., plastic, rubber, etc.

Collar 15e1 includes a first flange 15e2 and a second flange 15e3. Both first flange 15e2 and second flange 15e3 protrude radially, outside of handle 11, by extending through an opening in a side of handle 11. First flange 15e2 and second flange 15e3 may be either spaced apart by a gap laterally, or in contact with one another, closing the gap. These two configurations are discussed in further detail when referring to FIGS. 5B-5C. Furthermore, first flange 15e2 and second flange 15e3 each includes an opening that is aligned with the opening of the other.

Collar 15e1 further includes a locking pin 15e6 driven through first flange 15e2 and second flange 15e3, via their respective openings. Pin 15e6 may be of any suitable width or length that may fit into said openings and also remain in said openings when first flange 15e2 and second flange 15e3 are spaced apart. Flanges 15e2 and 15e3 may also slide laterally on pin 15e6 due to lateral forces exerted against flanges 15e2 and 15e3. Locking pin 15e6 includes a stop 15e4, coupled to one end of pin 15e6. Specifically, stop 15e4 is coupled to a first end of pin 15e6 that is nearest first flange 15e2. Stop 15e4 has a diameter greater than that of pin 15e6, as well as the flange opening of flange 15e2 through which pin 15e6 is driven. Thus, stop 15e4 prevents pin 15e6 from falling or sliding out of first flange 15e2.

Collar 15e1 also includes a lock handle 15e5. Lock handle 15e5 may be of any form, suitable for user actuation. Lock handle 15e5 is coupled to a second end of pin 15e6, adjacent to second flange 15e3. Handle 15e5 is configured to be pivotable about a pivot pin 15e7, which may be off-center of handle 15e5. Specifically, handle 15e5 is configured to pivot along the plane of collar 15e1, so that handle 15e5 may be pulled towards collar 15e1 or pulled away from collar 15e1 (see directional arrows of FIGS. 5B-5C).

As shown in FIG. 5B, first flange 15e2 and second flange 15e3 are spaced apart, along pin 15e6, thereby leaving collar 15e1 open, spaced from shaft 12, and loosened. This is the natural, unbiased shape of collar 15e1, as shown in FIG. 5B This configuration of lock 15e may be described as the unlocked configuration. In this state, collar 15e1 is loosened to an extent which allows for radial movement of shaft 12 within collar 15e1. Thus shaft 12 may be rotatable about a longitudinal axis of shaft 12 relative to handle 11 (not shown in FIG. 5B) in this loosened state. Handle 11 may also be rotatable about a longitudinal axis of handle 11 relative to shaft 12. It is noted that handle 15e5, in this unlocked configuration, is away from collar 15e1. However, as indicated by the directional arrows, pivoting handle 15e5 by pulling it towards collar 15e1 will result in collar 15e1 tightening onto shaft 12. This results in lock 15e being placed into a locked configuration, as further described below.

FIG. 5C shows lock 15e in a locked configuration. In this configuration, collar 15e1 is tightened onto shaft 12, thereby inhibiting any radial or rotational movement of shaft 12. Specifically, first flange 15e2 and second flange 15e3 are in contact with one another, closing any prior gap between the flanges (though it is not necessary for flanges 15e2 and 15e3 to contact for collar 15e1 to contact shaft 12). This is attributed to handle 15e5 being pivoted into a position towards collar 15e1. Pivoting handle 15e5, about pin 15e7, towards collar 15e1 results in a camming action. Specifically, as handle 15e5 pivots about pivot pin 15e7, outer surfaces of handle 15e5 press against an outer surface of flange 15e3 in a camming action, forcing flange 15e3 towards flange 15e2. The gap between flanges 15e2 and 15e3 continues to close until collar 15e1 contacts and closes around shaft 12, and any radial or longitudinal movement of shaft 12 is restricted. Such tightening onto shaft 12 places lock 15e in the locked configuration. Thus, to alternate between unlocking and locking lock 15e, handle 15e5 be pivoted so that it is pulled away or towards collar 15e1. Medical device 1e may be used in the same manner as medical device 1a, except a user may pivot lock handle 15e5, as described above, to unlock or lock the rotation of shaft 12, as opposed to rotating the collar.

Figure 6C:
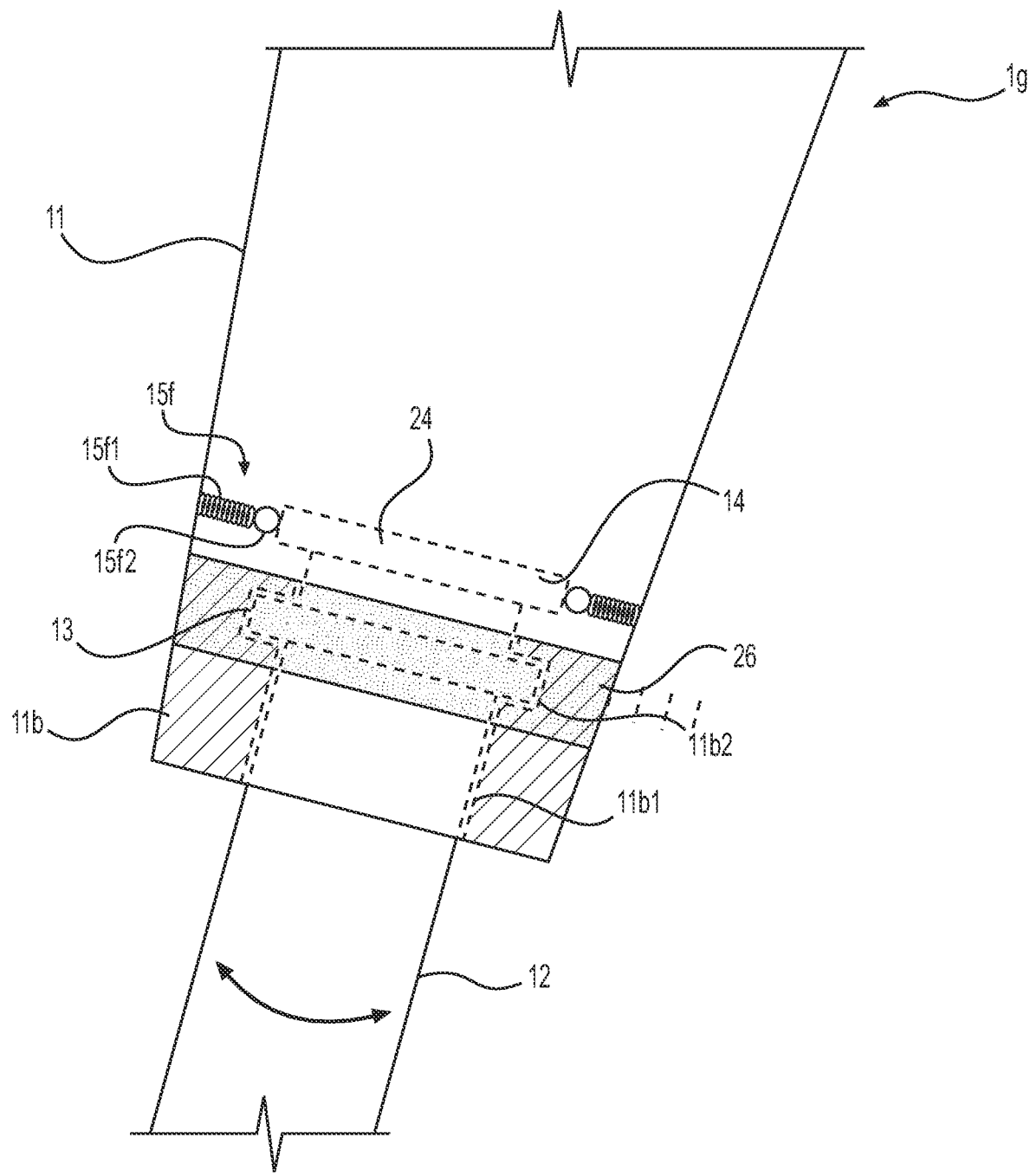
FIG. 6C is a perspective view of a portion of a medical device, according to another embodiment.

Medical device 1f, as shown in FIGS. 6A-6C, is similar to device 1b in many respects. Like reference numerals refer to like parts. Differences between device 1b and 1f will be described below. The inner wall of handle 11 includes a plurality of placeholders 15f. Placeholders 15f are circumferentially distributed along the inner wall of handle 11, and are evenly spaced apart. Placeholders 15f surround proximal flange 14', and are configured to engage with each of notches 24.

Each of placeholders 15f includes a spring 15f1 and a bearing 15f2. Spring 15f1 is coupled to an inner wall of handle 11 on one end. Bearing 15f2 is coupled to an opposite end of spring 15f1. Bearing 15f2 may be of any suitable form configured to engage with notches 24, each of which may be a specific, predetermined size that is receptive of bearing 15f2. Spring 15f1 may be any suitable spring having sufficient length so that bearings 15f2 may engage with each of notches 24. Furthermore, springs 15f1 may have spring forces that are sufficient so that typical in-procedure manipulation of medical device 1f does not result in unwanted disengagement of bearings 15f2 from notches 24.

The engagement of bearings 15f2 with notches 24 places lock 15f in a locked configuration. However, the aforementioned spring forces are also within the ergonomic capabilities of a user, and may be overcome by torsional forces exerted on shaft 12 by said user. Thus, a user may rotate shaft 12 so that bearings 15f2 are disengaged from notches 24, until bearings 15f2 re-engage with adjacent notches 24. Even after re-engagement, shaft 12 may continue to be rotated until bearings 15f2 re-engage notches 24 at a selected or predetermined rotational position of shaft 12. Thus, medical device 1f may be used in the same manner as medical device 1b, except a user may directly rotate shaft 12 by exerting torsional forces onto shaft 12 in any suitable manner.

Other embodiments may further include additional grips on shaft 12 to assist users in exerting sufficient torsional forces to rotate shaft 12. In some other embodiments, a rotatable dial 26 may be integrated into handle 11, as shown in FIG. 6C. Grip 26 may be fixed to shaft 12, for example at proximal flange 13, so that a user may grip and rotate dial 26 as opposed to gripping and rotating shaft 12.

In some other medical device embodiments, no lock or locking mechanism may be present and such embodiments may rely on frictional forces between the shaft and handle to hold relative position. Such frictional forces may be exerted by any suitable manner or mechanism, e.g., a frictional fit created by radial force or by material attraction properties.

Medical device 1h, as shown in FIGS. 7A-7B, is similar to previously described embodiments in many respects. Like reference numerals refer to like parts. However, the rotation of shaft 12 of medical device 1h is motorized, and the driver for rotation of shaft 12 also may serve as a lock. Driver 15h includes a switch 15h1 coupled to a servomotor 15h2. A portion of switch 15h1 is outside of handle 11, and actuatable by a user, while another portion of switch 15h1 extends through an opening in handle 11 into handle 11 Servomotor 15h2 is housed within handle 11. Servomotor 15h2 is coupled to a cam 15h3 configured to rotate and engage with notches 24 of proximal flange 14'. Servomotor 15h2 may turn on or off by actuation of switch 15h1, which may be of any suitable form.

The rotation of cam 15h3 by running servomotor 15h2, while cam 15h3 remains engaged with notches 24, rotates proximal flange 14', thereby rotating shaft 12 about a longitudinal axis of shaft 12 relative to handle 11. In contrast, a stationary cam 15h3, when servomotor 15h2 is not running, may lock shaft 12 in place as cam 15h3 remains engaged with notches 24, thereby inhibiting further rotation of shaft 12. Thus, medical device 1h may be used in the same manner as the previously described medical device embodiments, except a user may switch on/off driver 15h, via switch 15h1, to rotate or keep stationary shaft 12.

Figure 8A:
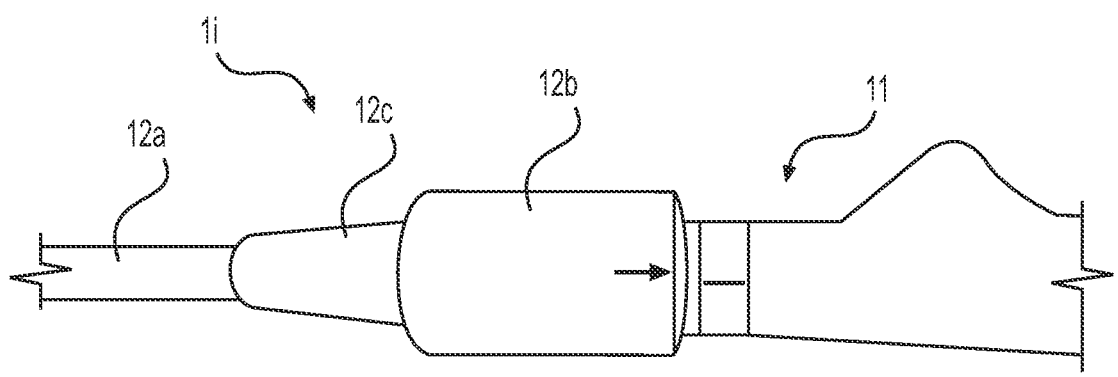
FIG. 8A is a perspective view of a portion of a medical device, according to another embodiment.
Figure 8B:
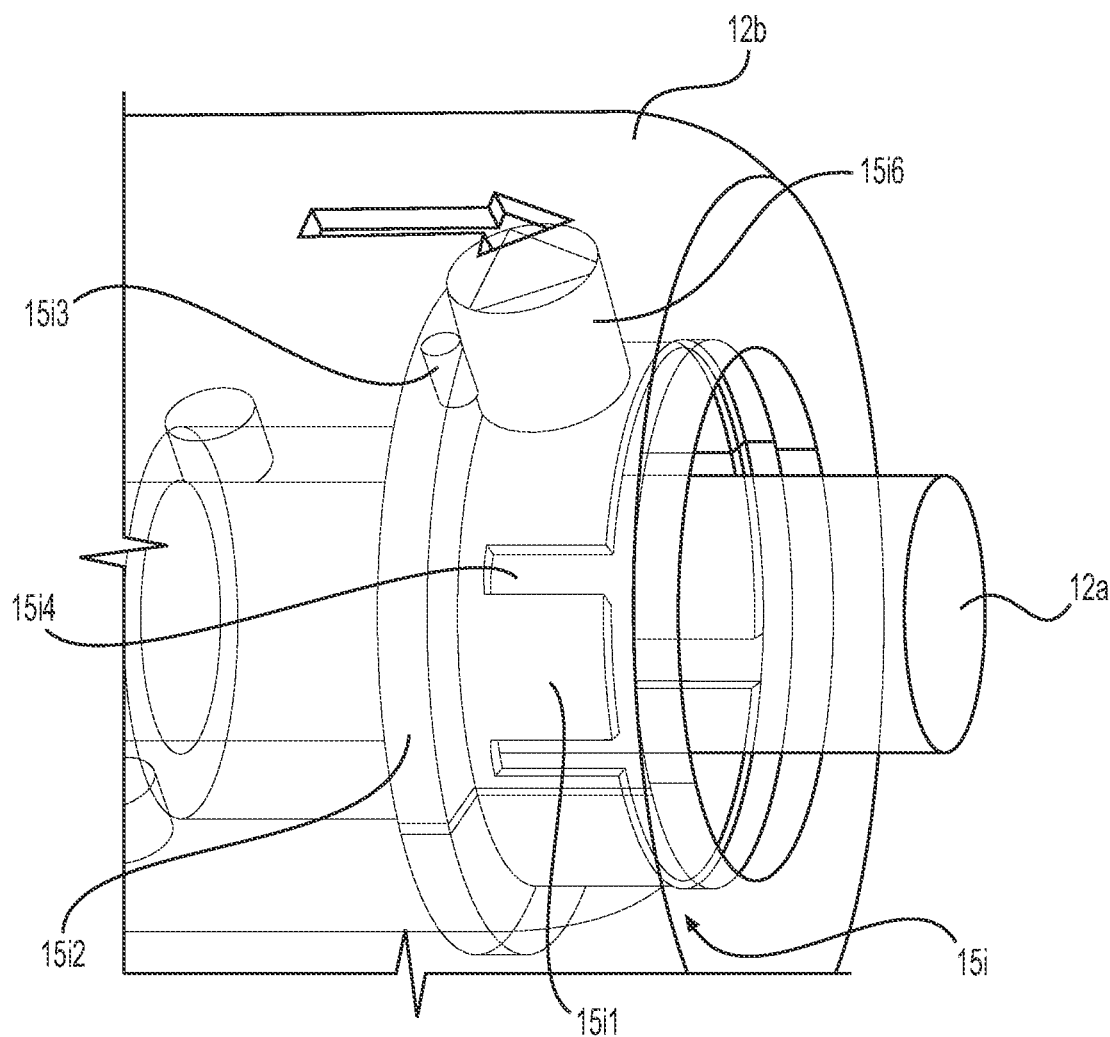
FIGS. 8B-8D are perspective views of a portion of the medical device of FIG. 8A.
Figure 8C:
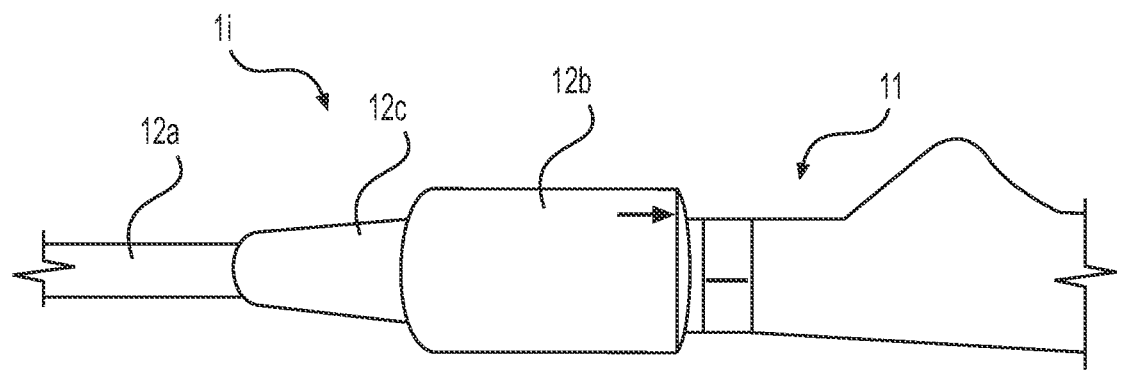

Medical device 1i, as shown in FIGS. 8A-8G, is similar to previously described device 1f in many respects. Like reference numerals refer to like parts. Differences between device 1i and device 1f will be described below. Medical device 1i includes handle 11, which is coupled to shaft 12a and a shaft housing 12b. Specifically, housing 12b houses a distal portion of handle 11. Shaft 12a and housing 12b may be rotatable about a longitudinal axis of shaft 12a relative to handle 11, as shown in FIGS. 8A and 8C.

Handle 11 and housing 12b include arrows indicating a starting rotational point of shaft 12 relative to handle 11 (see aligned arrows in FIG. 8A). Handle 11 and housing 12b may include any other suitable markings on their outer surfaces, in other embodiments. Referring to FIGS. 8B, 8D, 8E, and 8G, the inner surface of the distal end of handle 11 further includes a lock 15i. Lock 15i includes a ring 15i1, and a post 15i3. Ring 15i1 is annular in shape, and ring 15i1 includes a plurality of slots 15i4 evenly spaced apart, about the circumference of ring 15i1. Specifically, slots 15i4 are spaced apart in 45° intervals. Slots 15i4 are rectangular in shape, and extend distally from a proximal end of ring 15i1 to around a midpoint between the proximal end and the distal end of ring 15i1. Slots 15i4 are of a sufficient width to fit/anchor ball 15i5 of shaft housing 12, which is later described in further detail. However, it is noted that ring 15i1 is not limited as described, and may include more or less slots, different spacing, and different slot shapes. For example, as shown in FIGS. 8E and 8G, slots 15i4 may not be distributed throughout the whole circumference of ring 15i1. Post 15i3 is a cylindrical protrusion that is coupled onto a distal portion of ring 15i1. However, post 15i3 is not limited to being cylindrical, and may be of any suitable shape and/or dimension that may ride within a channel of housing 12b, as further described below.

Figure 8D:
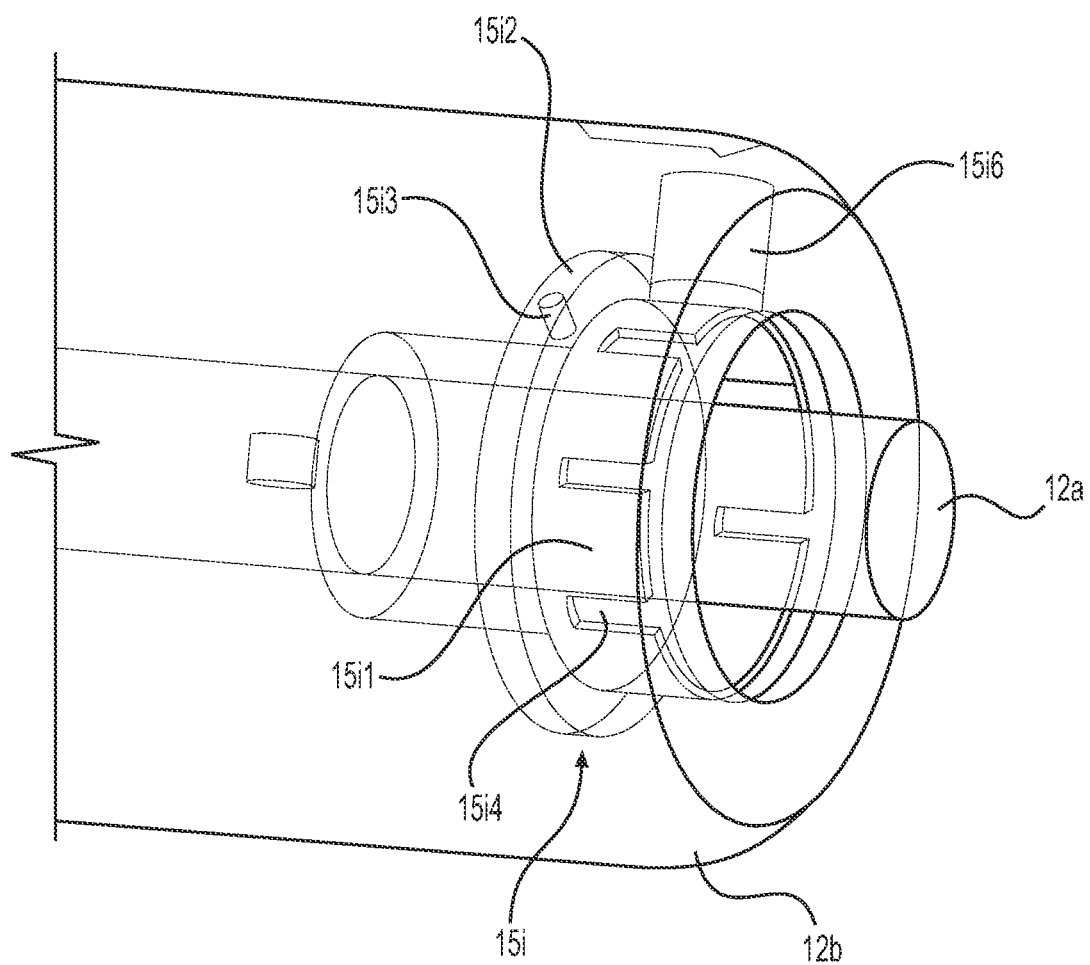
Figure 8E:
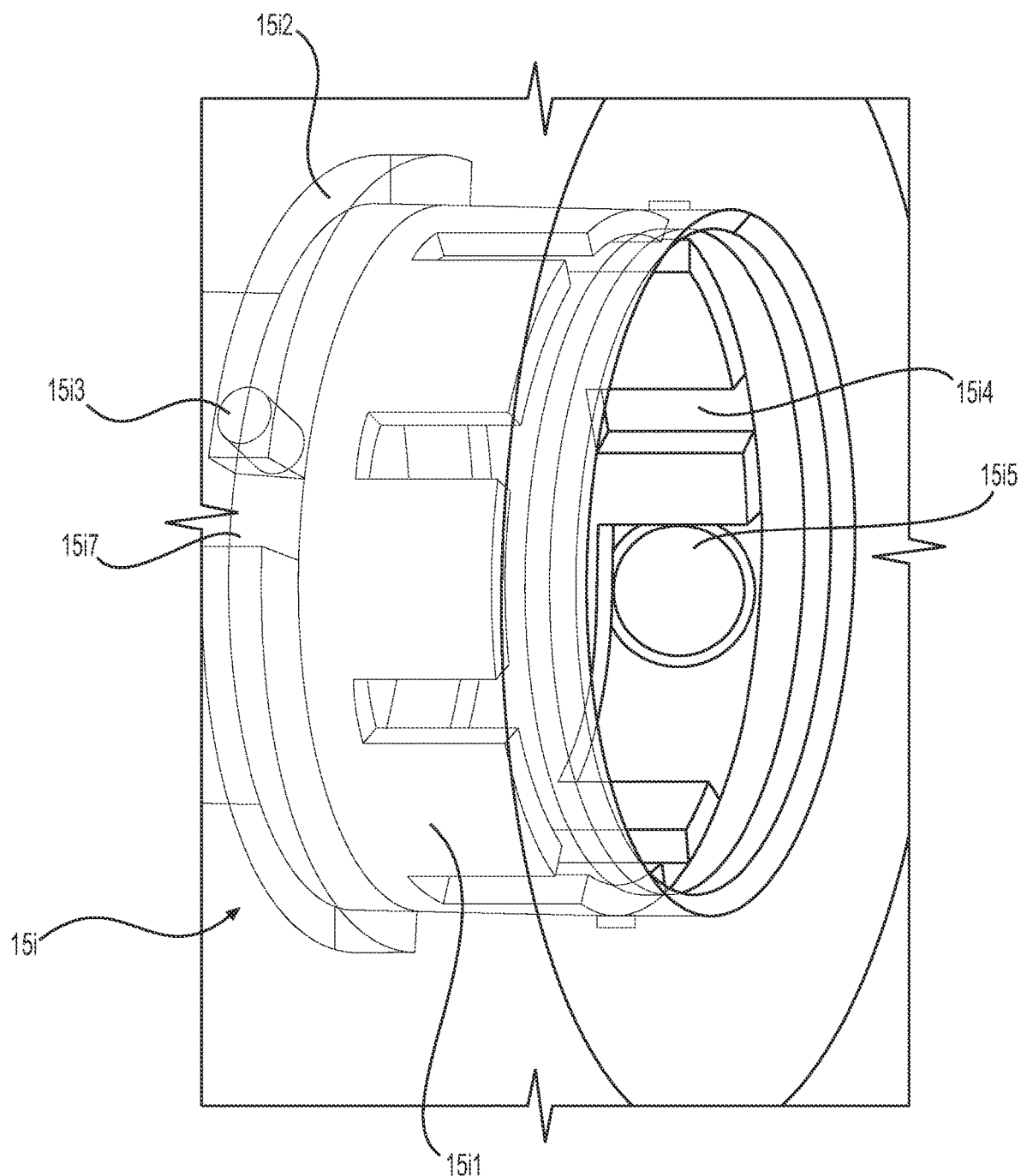
FIG. 8E is a perspective view of an inner lock of the medical device of FIG. 8A.
Figure 8G:
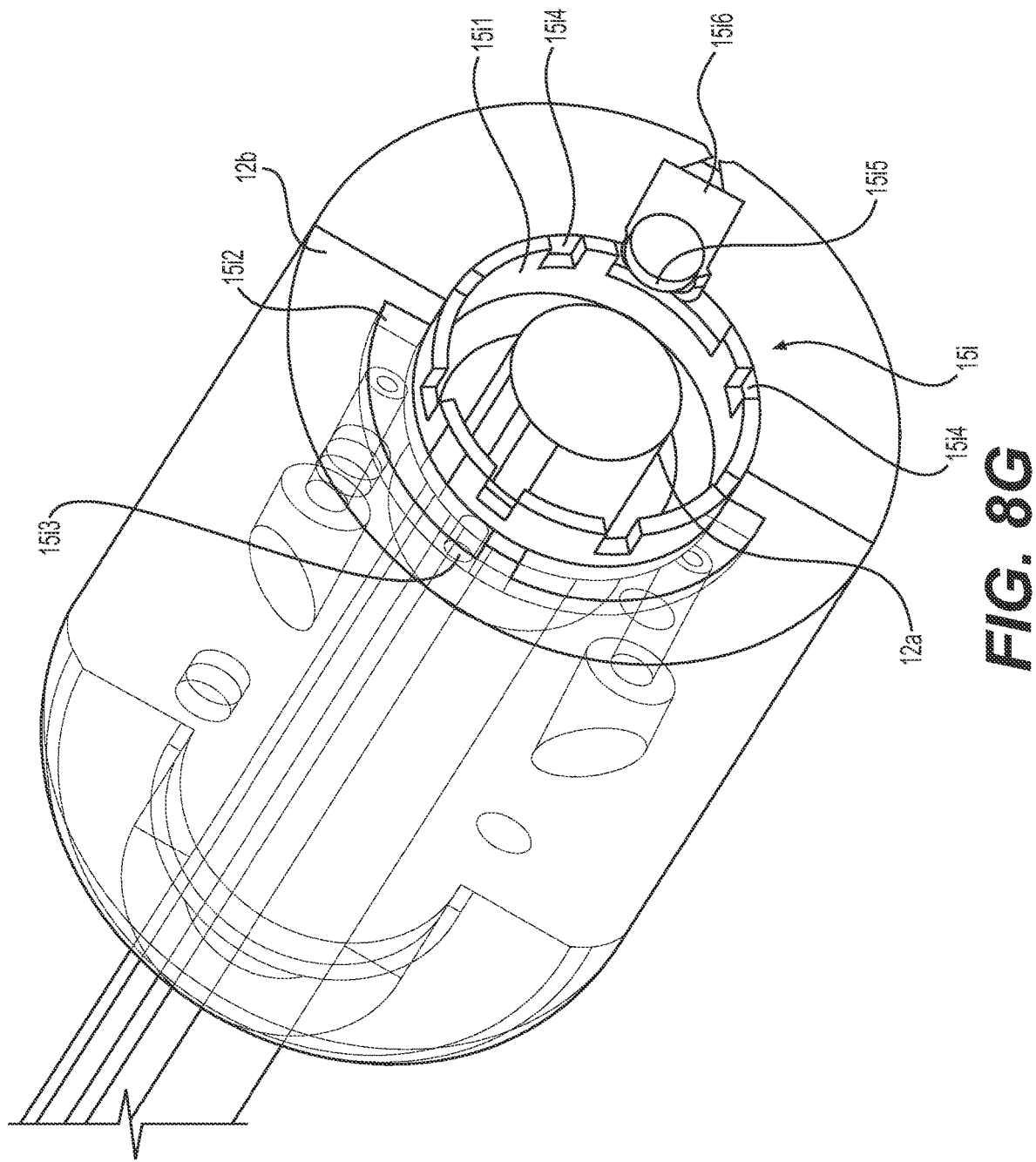
FIG. 8G is another perspective view of the inside of the medical device of FIG. 8A.

Referring to FIGS. 8B and 8D, a proximal portion of shaft 12a is housed by and fixed to housing 12b. Shaft 12a may be fixed to housing 12b by any suitable means, e.g., adhesion bonding, over-mold, and is not particularly limited. Therefore, shaft 12a and housing 12b rotate in unison, relative to handle 11. Shaft 12a exits housing 12b via an opening on a distal end of housing 12b. The distal end of housing 12b may also connect to a casing or strain relief 12c, which also covers a proximal portion of shaft 12a and from which shaft 12a may exit.

As shown in FIGS. 8A and 8C, housing 12b includes an arrow marking on its outer surface, around its proximal end. This arrow may be used as a reference to indicate the rotational position of housing 12b and shaft 12a, relative to handle 11 and its respective marking.

The inner proximal end of housing 12b further includes channel 15i2 and detent 15i6. Channel 15i2 is an annular/ring-like channel within a proximal portion of housing 12b. Channel 15i2 has no inner surface, and circumferentially encompasses the outer surface of the distal end of ring 15i1, such that channel 15i2 houses post 15i3. Thus, post 15i3 may ride within channel 15i2 as post 15i3 rotates along with ring 15i1, via rotation of handle 11, or channel 15i2 may rotate over post 15i3 via rotation of shaft housing 12b.

In some embodiments, channel 15i2 further includes a break or cutoff within its annular shape, so that a complete ring is not formed (see FIGS. 8E and 8G). This break may be described as a molded stop 15i7, as the break prevents post 15i3 from riding past either end of the break. For example, stop 15i7 may restrict rotation of detent 15i6 relative to handle 11, and vice versa, to a maximum of 175° in each rotational direction to prevent damage to internal structures. Because detent 15i6 is inhibited from rotation past a selected or predetermined degree, additional slots 15i4 on ring 15i1 may be unnecessary and thus not present for a portion of ring 15i1, as shown in FIGS. 8E and 8G. This break, i.e., molded stop 15i7, may be filled or occupied in some instances with other wires, components, etc.

As shown in FIGS. 8B and 8D, detent 15i6 is fixed to the inner surface of a proximal portion of housing 12b, so that as housing 12b rotates, detent 15i6 rotates as well. Detent 15i6 is a cylindrical housing radially extending from said inner surface to about or near ring 15i1 of handle 11. Detent 15i6 houses ball 15i5 (as shown in FIG. 8E) so that ball 15i5 partially protrudes from the end of housing 15i6 adjacent to ring 15i1. Thus, ball 15i5, which may be spring-loaded within detent 15i6, may engage with slots 15i4 of ring 15i5. Detent 15i6 is positioned adjacent to the proximal side of channel 15i2.

Ball 15i5 is partially housed in the end of detent 15i6 adjacent to ring 15i1, so that ball 15i5 may partially protrude out of that end. Ball 15i5 may be of any suitable size or shape that may engage with or anchor within slots 15*i*4. Furthermore ball 15*i*5 may be spring-loaded so that ball 15*i*5 retracts, via compression of a spring (not shown), when detent 15*i*6 is positioned over the outer surface of ring 15*i*5, via the rotation of handle 11 or shaft housing 12*b*. In instances when detent 15*i*6 is positioned over one of slots 15*i*4, ball 15*i*5 may protrude out of the end of detent 15*i*6, via extension of the spring, so that ball 15*i*5 may be anchored within the slot 15*i*4. This anchoring of detent ball 15*i*5 may be described as a locked configuration of device 1*i*. In said locked configuration, further rotation of shaft 12*a* and housing 12*b* is inhibited, until sufficient rotational forces are applied against shaft handle 12*b* relative to handle 11. Thus, medical device 1*i* may be used in the same manner as previously described medical device embodiment 1*f*, except rotation of shaft 12*a* and handle 12*b* may be restricted to a selected or predetermined rotational degree due to stop 15*i*7.

Figure 9A:
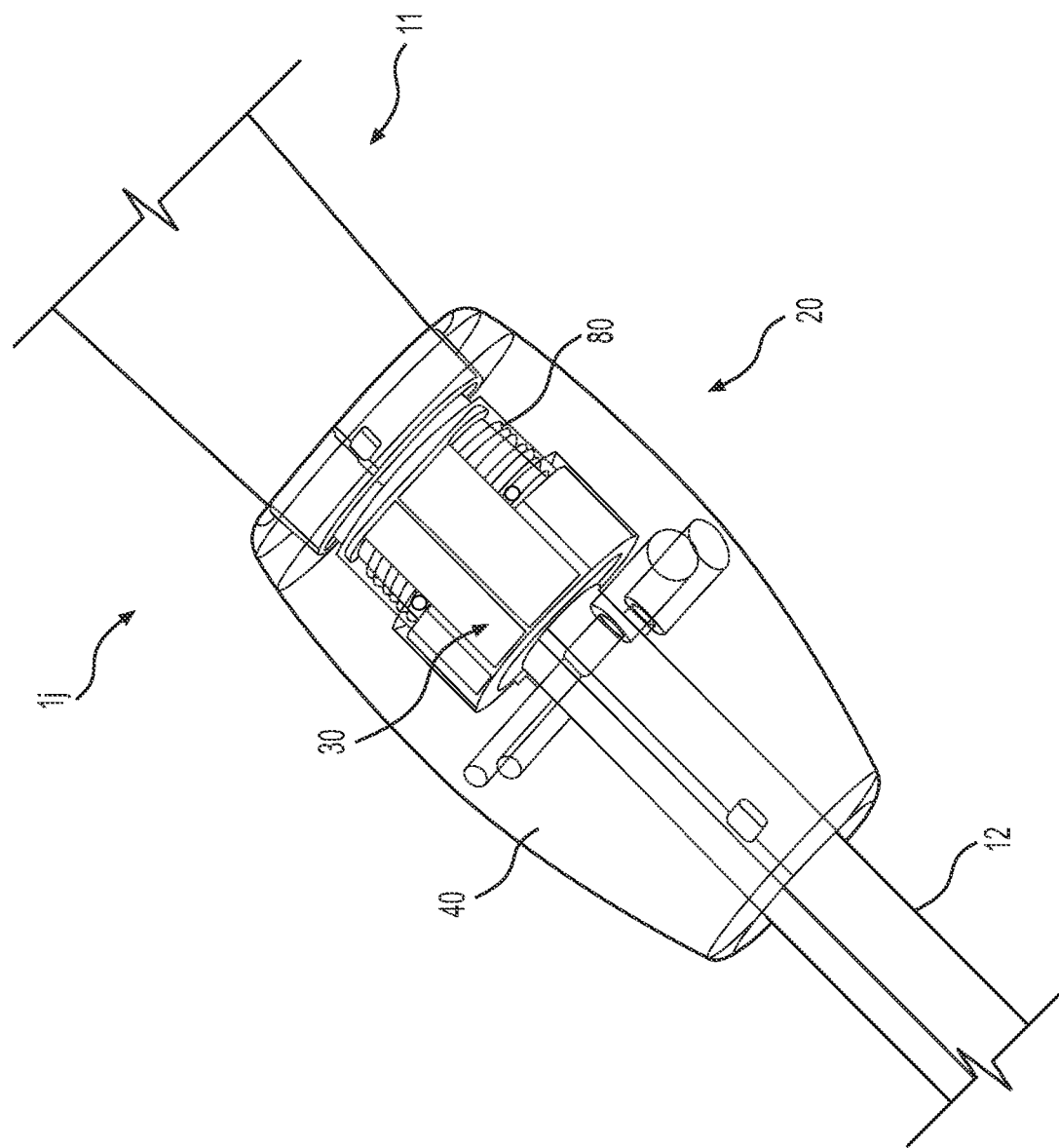
FIGS. 9A-9B are perspective views of a portion of a medical device, according to another embodiment.
Figure 9B:
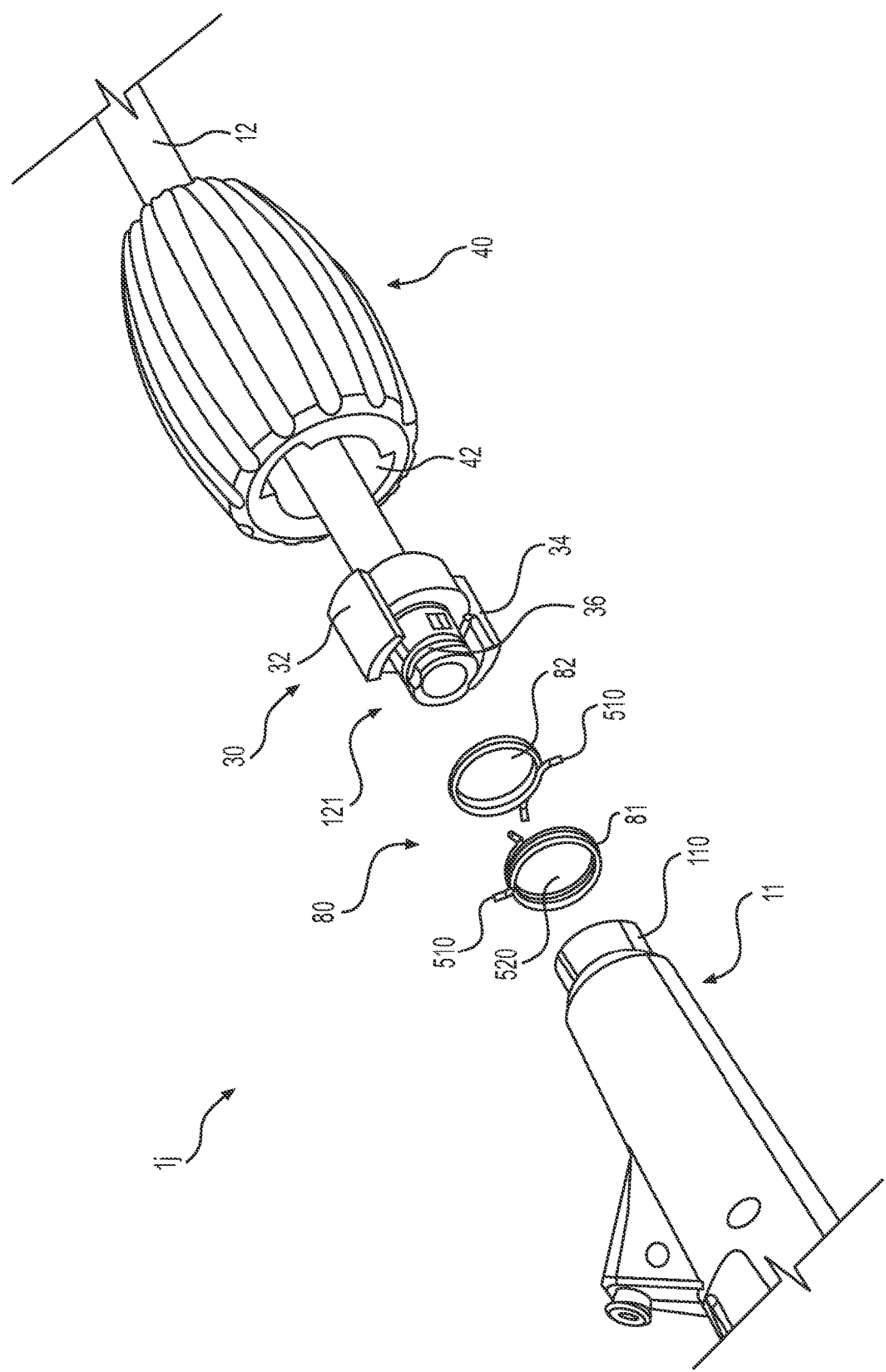
Figure 9C:
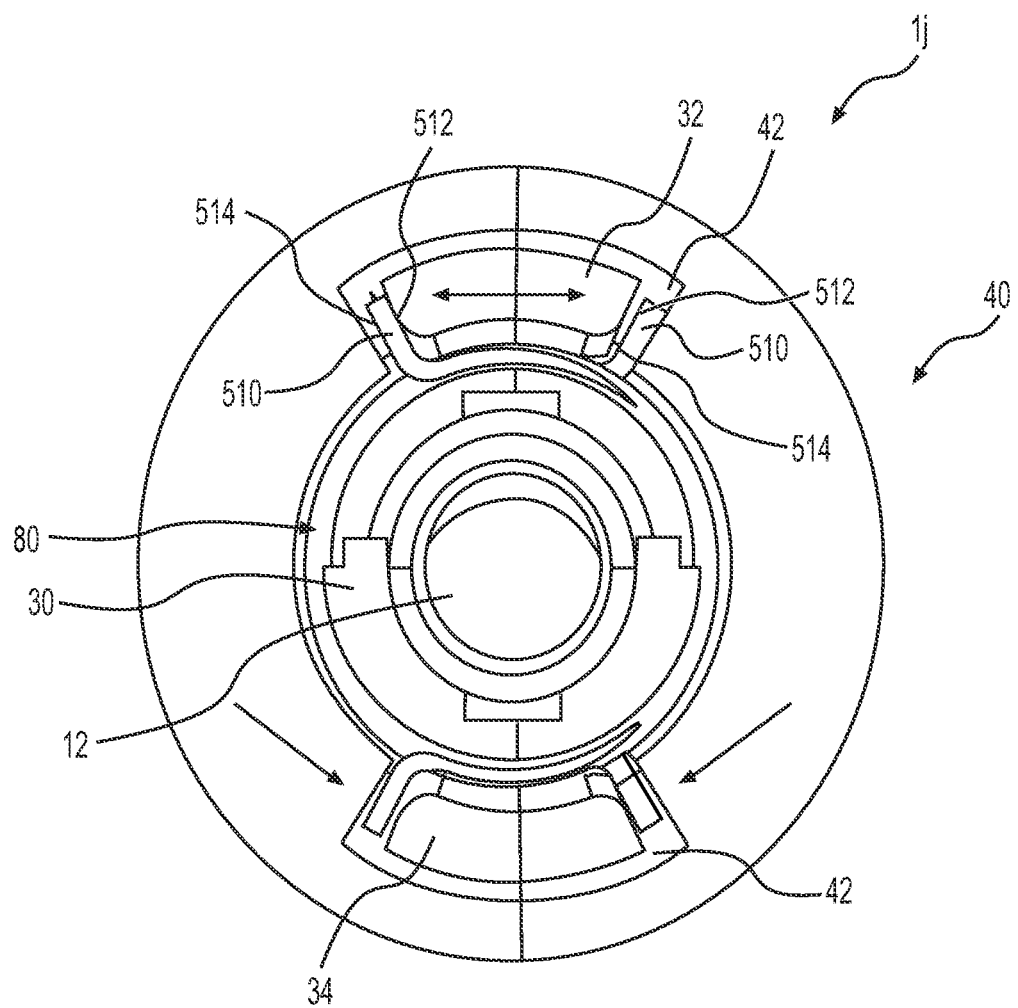
FIG. 9C is a cross-sectional view of the medical device of FIGS. 9A-9B.

Medical device 1*j*, as shown in FIGS. 9A-9C, is similar to previously described embodiments in many respects. Like reference numerals refer to like parts. As discussed in prior embodiments, handle 11 may be rotatably coupled to shaft 12, so that handle 11 may rotate about a longitudinal axis of device 1*j*, relative shaft 12, and vice versa. The manner in which handle 11 and shaft 12 are rotatably coupled is not particularly limited. For example, in some embodiments, a proximal portion 121 of shaft 12 may include a channel or recess 36 (shown in FIG. 9B) extending along the circumference of shaft 12. Channel 36 may receive a protrusion (not shown) extending radially inwards within a distal portion of handle 11, which may ride within channel 36 as handle 11 or shaft 12 is rotated relative to the other.

Figure 9D:
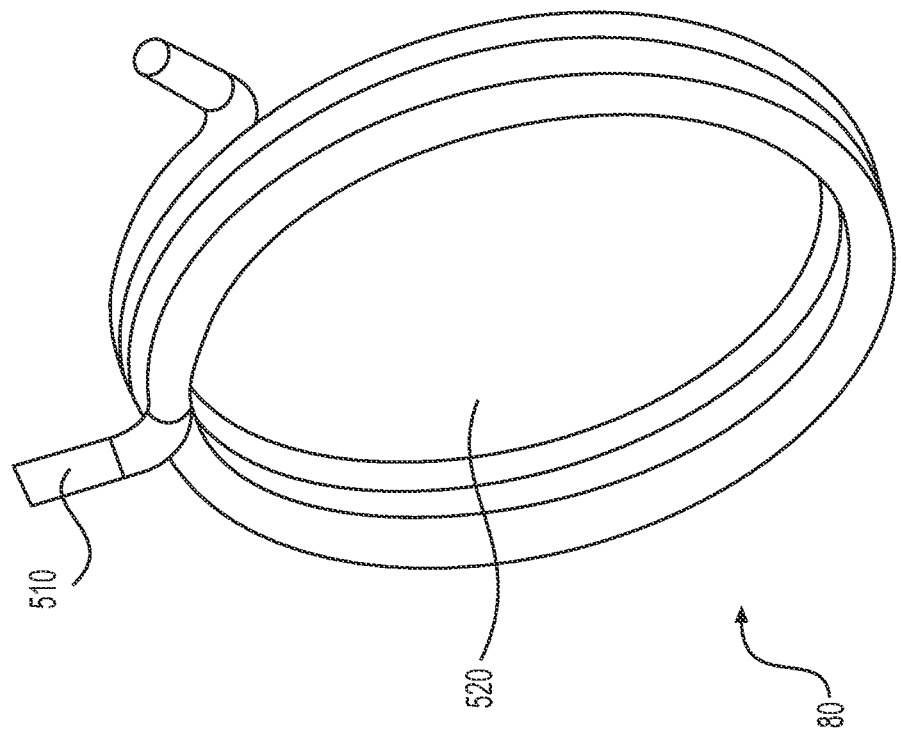
FIG. 9D is a perspective view of a resistance feature of the medical device of FIGS. 9A-9C.

In addition to handle 11 and shaft 12, medical device 1*j* further includes a rotating feature 20, which comprises resistance components 80, locking component 30, and a grip 40. Device 1*j* includes two resistance components 80, a first spring 81 and a second spring 82 (see e.g., FIG. 9D). However, it is noted that the number of resistance components is not particularly limited, e.g., one, three, four, etc. Both springs 81 and 82 may be coil springs defining central openings 520. Moreover, each of the two ends of both springs 81 and 82 includes a post 510 that extends radially outwards from springs 81 and 82. The size and number of loops of springs 81 and 82 is not particularly limited, and may be based on the amount of torque being transmitted via springs 81 and 82. As shown in FIGS. 9A and 9B, springs 81 and 82 may be frictionally fitted around a distal portion 110 of handle 11 via central openings 520. Thus, based on such configuration, a force applied against an inner surface 512 of post 510 (a surface closest to the adjacent post 510) pushes posts 510 away from each other, reduces a size of central openings 520, and results in springs 81, 82 coiling tighter around distal portion 110, thereby increasing the amount of torque that may be driven via such connection. In contrast, a force applied against an outer surface 514 of post 510 (a surface furthest from the adjacent post 510) pushes posts 510 toward each other, increases a size of central openings 520, and results in springs 81, 82 uncoiling, thereby resulting in springs 81, 82 loosening and slipping on distal portion 110. It is noted that the orientation of posts 510 of spring 81, relative to posts 510 of spring 82, is not particularly limited, and may depend on the positioning of tabs 32, 34, as further discussed below.

Locking component 30 may be an annular piece including a central opening, a first tab 32, a second tab 34, and a channel 36. Said central opening may be an opening of a sufficient diameter or width to receive shaft 12, such that the surface defining of the central opening may be flush against the outer surface of shaft 12. First and second tabs 32, 34 may be features extending proximally from an edge of component 30. First and second tabs 32, 34 are configured to engage with springs 81 and 82. Thus, tabs 32, 34 may be of a sufficient width to be keyed within the gaps between posts 510 of springs 81 and 82, as shown in FIG. 9C. Furthermore, tabs 32, 34 may be of a width that minimizes clearance between inner surfaces 512 of posts 510 and tabs 32, 34. As shown in FIGS. 9B-9C, tabs 32, 34 may be on opposite sides of locking component 30 (approximately 180° apart), but is not limited thereto. Moreover, it is noted that locking component 30, via its central opening, may be immovably fixed around a proximal portion 121 of shaft 12. The manner in which locking component 30 is immovably fixed to shaft 12 is not particularly limited (e.g., glue, adhesive, welding, etc.).

Grip 40 is a graspable feature sheathing a proximal portion of shaft 12, locking component 30, and springs 81, 82. Grip 40 includes a proximal opening 42, a distal opening (not shown), and a lumen defined therebetween. Proximal opening 42 is configured to receive locking component 30 and springs 81, 82. Proximal opening 42 is in the shape of locking component 30 and springs 81, 82, so that locking component 30 and springs 81, 82 may key into grip 40. Thus, opening 42 and a portion of the lumen of grip 40 may surround the contour of locking component 30 and springs 81, 82, as shown in FIGS. 9B-9C. Grip 40 may surround locking component 30 and springs 81, 82, while minimizing the clearance between the inner surface of grip 40 and outer surfaces 514 of posts 510, as shown in FIG. 9C. However, it is noted that grip 40 may be rotatable relative to shaft 12, so that the inner surface of grip 40 may interface with outer surfaces 514 of posts 510. Grip 40 further includes a distal opening (not shown) through which shaft 12 extends distally. Said distal opening may be of any suitable diameter that allows for frictional fit around shaft 12, so that grip 40 may maintain its position along the length of shaft 12.

In view of the above-described configuration, shaft 12, by default, may be locked in a rotational position when a user does not apply any rotational forces on handle 11, shaft 12, or grip 40, relative to one another. Any rotation, clockwise or counter-clockwise, of shaft 12 relative to handle 11 results in tabs 32 and 34 of locking component 30 applying a force against inner surfaces 512 of posts 510. Such a force causes springs 81, 82 to coil tighter about distal portion 110 of handle 11 through the natural motion of applying torque to shaft 12 through handle 11. This effectively locks the rotation of handle 11 or shaft 12 relative to the other. To adjust the rotational position of handle 11 to shaft 12, and vice versa, grip 40 may be adjusted or held in place so that the inner surface of grip 40 may apply a force against the outer surfaces 514 of springs 81 and 82. Such a force causes springs 81, 82 to uncoil about distal portion 110 of handle 11, thereby enabling the rotation of handle 11 relative to shaft 12 (and vice versa). After reaching a desired rotational position, grip 40 may be released, which causes springs 81, 82 to revert to their natural bias, holding shaft 12 relative to handle 11 in the new position. As a result, locking component 30 may naturally "lock" via the release of grip 40. Thus, medical device 1*j* may be used in the same manner as the previously described medical device embodiments, except a user may hold grip 40 while adjusting the rotational position of handle 11 relative to shaft 12 (or vice versa).

It is noted that in another exemplary embodiment, coil springs, e.g., springs 81 and 82, may be frictionally fitted around shaft 12, with posts 510 interacting with features of handle 11 and grip 40. Said features of handle 11 may be similar in shape and function as tabs 32 and 34 of locking component 30. Such an embodiment may function in a similar manner as device 1j, except shaft 12 may be rotated/manipulated relative to grip 40.

Resistance components 80 are not limited to coil springs 81, 82, as shown in FIGS. 9A-9C. In other exemplary embodiments, the springs may include posts extending radially inwards, or the spring wires may be of a square or rectangular cross section. Moreover, the springs may be in any number of whole or partial wraps such that the amount of friction increases when pressure is applied to posts 510 in one direction (e.g., against surface 512) and decreases when applied to posts 510 in the other direction (e.g., against surface 514). Posts 510, on each end of a spring, may also occur at less than or greater than 360° of wrap. Furthermore, other similarly-functioning resistance components may be utilized in place of springs 81, 82, e.g., hose clamps. However, some similarly-functioning resistance components may require adjustments to the above-described configuration of rotating feature 20, for the device to function in the same manner. For example, depending on the manner in which alternative resistance components tighten or loosen, said resistance components may be fitted onto a handle differently, or differently shaped locking components may be needed.

Figure 10:
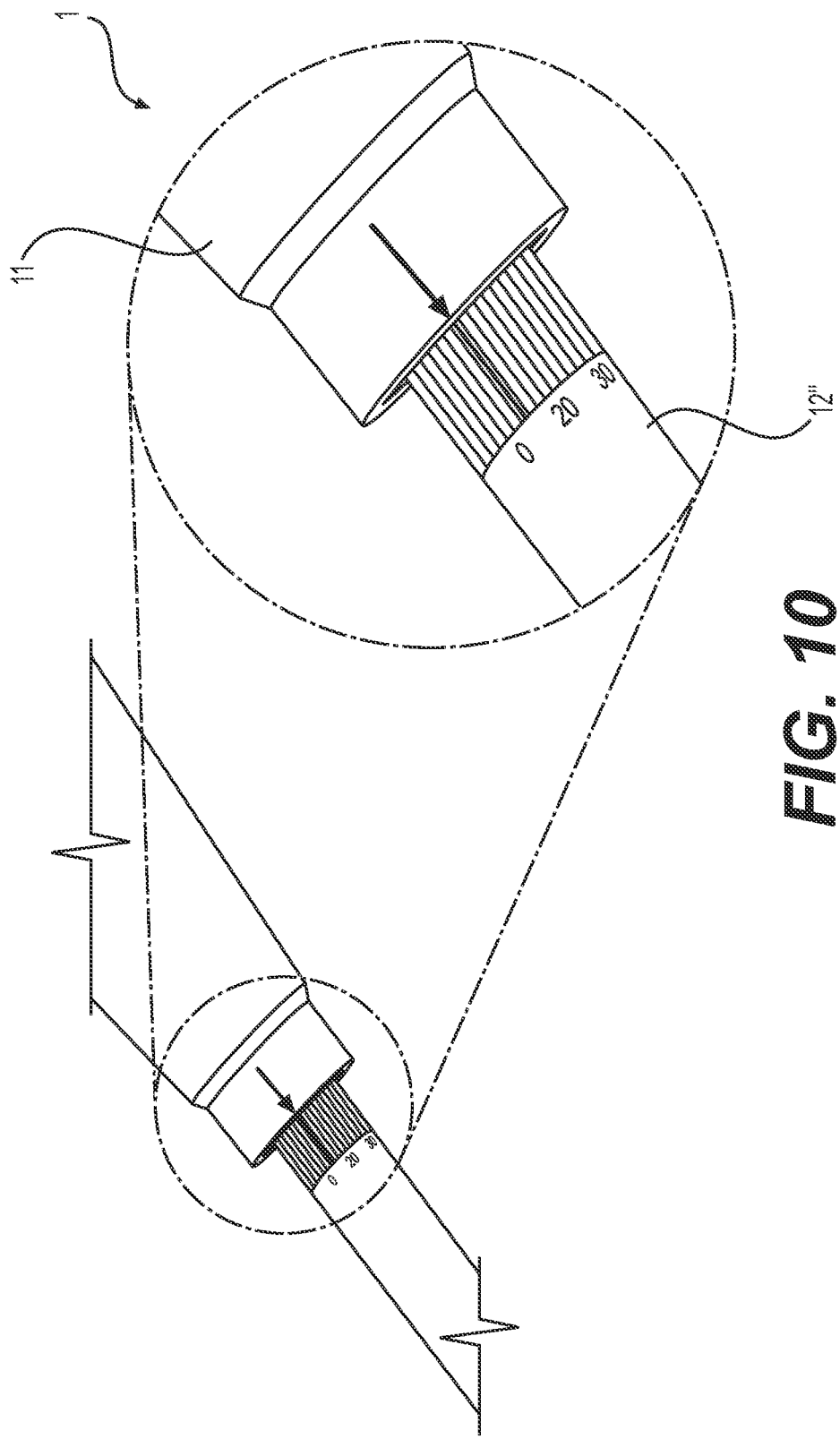
FIG. 10 is a perspective view of a portion of a medical device, according to another embodiment.

FIG. 10 shows an embodiment of medical device 1 wherein shaft 12" includes incremental markings to assist a user in determining the rotational position of shaft 12" relative to handle 11. In other embodiments, handle 11 may also, or alternatively, include markings to help a user gauge the rotational position of shaft 12. The markings in FIG. 10 indicate a numeric degree of rotation relative to the arrow marking provided on a distal end of handle 11. However, markings are not limited to the examples provided in FIG. 10. Markings are not particularly limited, and may include various combinations of numbers, letters, or words, indicating rotation of shaft 12" relative to handle 11, and vice versa. It is noted that such markings may also be applied to any of the previously described medical device embodiments.

It will be apparent to those skilled in the art that various modifications and variations can be made to the disclosed device without departing from the scope of the disclosure. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical device comprising:
   a shaft;
   a handle housing a proximal portion of the shaft; and
   a lock having a first configuration and a second configuration;
   wherein, in the first configuration of the lock, the shaft is rotatable about a longitudinal axis of the shaft relative to the handle, and, in the second configuration of the lock, the shaft is stationary relative to the handle,
   wherein the lock includes a collar and a plurality of deflectors,
   wherein the plurality of deflectors surround the proximal portion of the shaft,
   wherein the collar surrounds the plurality of deflectors and the proximal portion of the shaft,
   wherein the collar includes a plurality of projections that project radially inward toward a longitudinal axis of the handle,
   wherein rotation of the collar in a first direction places the lock into the first configuration, and wherein rotation of the collar in a second direction opposite to the first direction places the lock into the second configuration,
   wherein the shaft includes a proximal flange and a distal flange, wherein a portion of the shaft positioned between the proximal flange and the distal flange includes a diameter, wherein the diameter of the portion of the shaft is lesser than a diameter of the distal flange and is lesser than a diameter of the proximal flange, and
   wherein, when the collar is in the second configuration, each deflector of the plurality of deflectors is pressed against the proximal flange.

2. The medical device of claim 1, wherein in the second configuration, engagement of the plurality of deflectors to the shaft provides sufficient friction force to keep the shaft stationary relative to the handle.

3. The medical device of claim 1, wherein the plurality of deflectors connect a proximal portion of the handle to a distal portion of the handle.

4. The medical device of claim 1, wherein the plurality of projections project from an inner circumferential surface of the collar.

5. The medical device of claim 1, wherein, in the first configuration, the plurality of projections of the collar is spaced apart from the plurality of deflectors allowing radial movement of the plurality of deflectors between the collar and the shaft, and wherein, in the second configuration, the plurality of projections pushes the plurality of deflectors against the shaft so that the shaft is held stationary relative to the handle.

6. The medical device of claim 5, wherein the plurality of deflectors flex radially inward toward the shaft in the second configuration.

7. A method of positioning a shaft of a medical device, comprising:
   inserting a distal end of the shaft of the medical device into a body of a subject, wherein the medical device comprises the shaft, a handle housing a proximal portion of the shaft, and a lock having a first configuration and a second configuration, wherein in the first configuration of the lock, the shaft is rotatable about a longitudinal axis of the shaft relative to the handle, and, in the second configuration of the lock, the shaft is stationary relative to the handle, wherein the lock includes a collar, a plurality of deflectors, and a plurality of projections, wherein the shaft includes a proximal flange and a distal flange, wherein a portion of the shaft positioned between the proximal flange and the distal flange includes a diameter, wherein the diameter of the portion of the shaft is lesser than a diameter of the distal flange and is lesser than a diameter of the proximal flange, wherein, when the collar is in the second configuration, each deflector of the plurality of deflectors is pressed against the proximal flange, and
   after the insertion step:
   unlocking the handle from the shaft by rotating the collar in a first direction, wherein rotating the collar in the first direction disengages the plurality of deflectors from the plurality of projections;
   rotating the shaft about the longitudinal axis of the shaft relative to the handle; and
   locking the handle to the shaft by rotating the collar in a second direction opposite to the first direction, such that the plurality of deflectors engage with the plurality of projections, wherein the plurality of deflectors is pressed radially inward toward the longitudinal axis of the shaft by the plurality of projections.

8. The method of claim 7, wherein engagement of the plurality of deflectors with the plurality of projections applies a frictional force to the shaft.

9. The method of claim 7, wherein the plurality of deflectors extend longitudinally from a proximal portion of the handle to a distal portion of the handle.

10. The method of claim 7, wherein the plurality of projections are positioned relative to the plurality of deflectors so that rotating the collar in the second direction facilitates engagement of corresponding complementary surfaces of the plurality of projections and the plurality of deflectors.

11. A medical device comprising:
a shaft;
a handle housing a proximal portion of the shaft; and
a lock having a first configuration and a second configuration;
wherein, in the first configuration of the lock, the shaft is rotatable about a longitudinal axis of the shaft relative to the handle, and, in the second configuration of the lock, the shaft is stationary relative to the handle,
wherein the lock includes a collar and a plurality of deflectors,
wherein the plurality of deflectors connect a proximal portion of the handle to a distal portion of the handle,
wherein the shaft includes a proximal flange and a distal flange, wherein a portion of the shaft positioned between the proximal flange and the distal flange includes a diameter, wherein the diameter of the portion of the shaft is lesser than a diameter of the distal flange and is lesser than a diameter of the proximal flange, and
wherein, when the collar is in the second configuration, each deflector of the plurality of deflectors is pressed against the proximal flange.

12. The medical device of claim 11, wherein the plurality of deflectors extend longitudinally from the proximal portion of the handle to the distal portion of the handle.

13. The medical device of claim 12, wherein the collar includes a plurality of projections that project radially inward toward the shaft, wherein, in the first configuration, each of the plurality of projections of the collar is spaced apart from the plurality of deflectors allowing radial movement of the plurality of deflectors between the collar and the shaft, and wherein, in the second configuration, the plurality of projections pushes each of the plurality of deflectors against the shaft so that the shaft is held stationary relative to the handle.

14. The medical device of claim 13, wherein the plurality of deflectors flex radially inward toward the shaft in the second configuration.

15. The medical device of claim 14, wherein the plurality of deflectors are not flexed radially inward toward the shaft in the first configuration.

16. The medical device of claim 13, wherein the plurality of projections and the plurality of deflectors include complementary surfaces to one another.

17. The medical device of claim 13, wherein the plurality of deflectors provide frictional force to the shaft in the second configuration.

* * * * *